US009833214B2

(12) United States Patent
Imamura

(10) Patent No.: US 9,833,214 B2
(45) Date of Patent: Dec. 5, 2017

(54) RADIOGRAPHIC IMAGE CAPTURING DEVICE, METHOD FOR DETECTING RADIATION DOSES, AND COMPUTER READABLE STORAGE MEDIUM

(71) Applicant: FUJIFILM CORPORATION, Minato-ku, Tokyo (JP)

(72) Inventor: Ryou Imamura, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 478 days.

(21) Appl. No.: 14/620,208

(22) Filed: Feb. 12, 2015

(65) Prior Publication Data
US 2015/0153464 A1 Jun. 4, 2015

Related U.S. Application Data

(63) Continuation of application No. PCT/JP2013/074433, filed on Sep. 10, 2013.

(30) Foreign Application Priority Data

Sep. 28, 2012 (JP) .................................. 2012-218258

(51) Int. Cl.
*H01L 27/146* (2006.01)
*H01L 27/148* (2006.01)
(Continued)

(52) U.S. Cl.
CPC ................ *A61B 6/586* (2013.01); *A61B 6/58* (2013.01); *G01T 7/005* (2013.01);
(Continued)

(58) Field of Classification Search
CPC ........... A61B 6/00; A61B 6/42; A61B 6/4208; A61B 6/4233; A61B 6/58; A61B 6/586;
(Continued)

(56) References Cited

U.S. PATENT DOCUMENTS

2008/0205747 A1* 8/2008 Kuchii ...................... G06T 5/20
382/149
2008/0230708 A1* 9/2008 Enomoto ............... G01T 1/2018
250/370.08
(Continued)

FOREIGN PATENT DOCUMENTS

JP 2012-015913 A 1/2012

*Primary Examiner* — Anastasia Midkiff
(74) *Attorney, Agent, or Firm* — Solaris Intellectual Property Group, PLLC

(57) ABSTRACT

A radiographic image capturing device includes: plural radiation dose detection pixels that respectively output signal values according to a dose of irradiated radiation; a determination unit that determines a presence or absence of defects, block-by-block, based on signal values of radiation dose detection pixels included in each of plural blocks, which are arranged such that the respective blocks include at least a portion of the plural radiation dose detection pixels; a block rearrangement unit that performs block rearrangement to change the arrangement of the plural blocks according to a determination result of the determination unit; and a detection unit that detects a dose of irradiated radiation based on signal values of each arranged block or of each rearranged block.

12 Claims, 25 Drawing Sheets

(51) Int. Cl.
*A61B 6/00* (2006.01)
*H01J 37/22* (2006.01)
*G01T 1/02* (2006.01)
*G06T 7/00* (2017.01)
*G01T 7/00* (2006.01)
*H01L 27/144* (2006.01)
*H04N 5/32* (2006.01)

(52) U.S. Cl.
CPC .. H01L 27/14605 (2013.01); H01L 27/14607 (2013.01); H01L 27/14812 (2013.01); *A61B 6/4283* (2013.01); *A61B 6/542* (2013.01); *A61B 2560/0276* (2013.01); *A61B 2562/046* (2013.01); *G01T 1/026* (2013.01); *G06T 7/0012* (2013.01); *G06T 2207/20221* (2013.01); *H01J 2237/24465* (2013.01); *H01J 2237/24507* (2013.01); *H01J 2237/24592* (2013.01); *H01L 27/1446* (2013.01); *H01L 27/14806* (2013.01); *H04N 5/32* (2013.01)

(58) Field of Classification Search
CPC ........ A61B 2560/00; A61B 2560/0266; A61B 2560/0276; A61B 2562/00; A61B 2562/02; A61B 2562/04; A61B 2562/046; G01T 1/00; G01T 1/02; G01T 1/023; G01T 1/026; G01T 1/16; G01T 1/161; G01T 7/00; G01T 7/005; G06T 1/00; G06T 1/0007; G06T 7/00; G06T 7/0002; G06T 7/0012; G06T 7/0014; G06T 2207/00; G06T 2207/10; G06T 2207/10072; G06T 2207/10081; G06T 2207/10116; G06T 2207/20; G06T 2207/20021; G06T 2210/00; G06T 2210/41; G06T 2211/00; G06T 2211/40; H01J 37/00; H01J 37/22; H01J 37/222; H01J 37/244; H01J 2237/00; H01J 2237/244; H01J 2237/2441; H01J 2237/24415; H01J 2237/2443; H01J 2237/2445; H01J 2237/2446; H01J 2237/24465; H01J 2237/245; H01J 2237/24507; H01J 2237/24592; H01L 27/14; H01L 27/142; H01L 27/144; H01L 27/1446; H01L 27/146; H01L 27/14601; H01L 27/14603; H01L 27/14605; H01L 27/14607; H01L 27/14643; H01L 27/14658; H01L 27/14659; H01L 27/14661; H01L 27/14663; H01L 27/14665; H01L 27/14676; H01L 27/148; H01L 27/14806; H01L 27/14812

See application file for complete search history.

(56) References Cited

U.S. PATENT DOCUMENTS

| | | | | |
|---|---|---|---|---|
| 2011/0049374 | A1* | 3/2011 | Omi | G09G 3/006 250/370.08 |
| 2011/0110497 | A1* | 5/2011 | Nishino | A61B 6/04 378/98.8 |
| 2012/0001079 | A1* | 1/2012 | Okada | H04N 5/32 250/366 |
| 2012/0305791 | A1* | 12/2012 | Watanabe | G01T 1/247 250/394 |
| 2013/0208852 | A1* | 8/2013 | Koishi | A61B 6/032 378/19 |

* cited by examiner

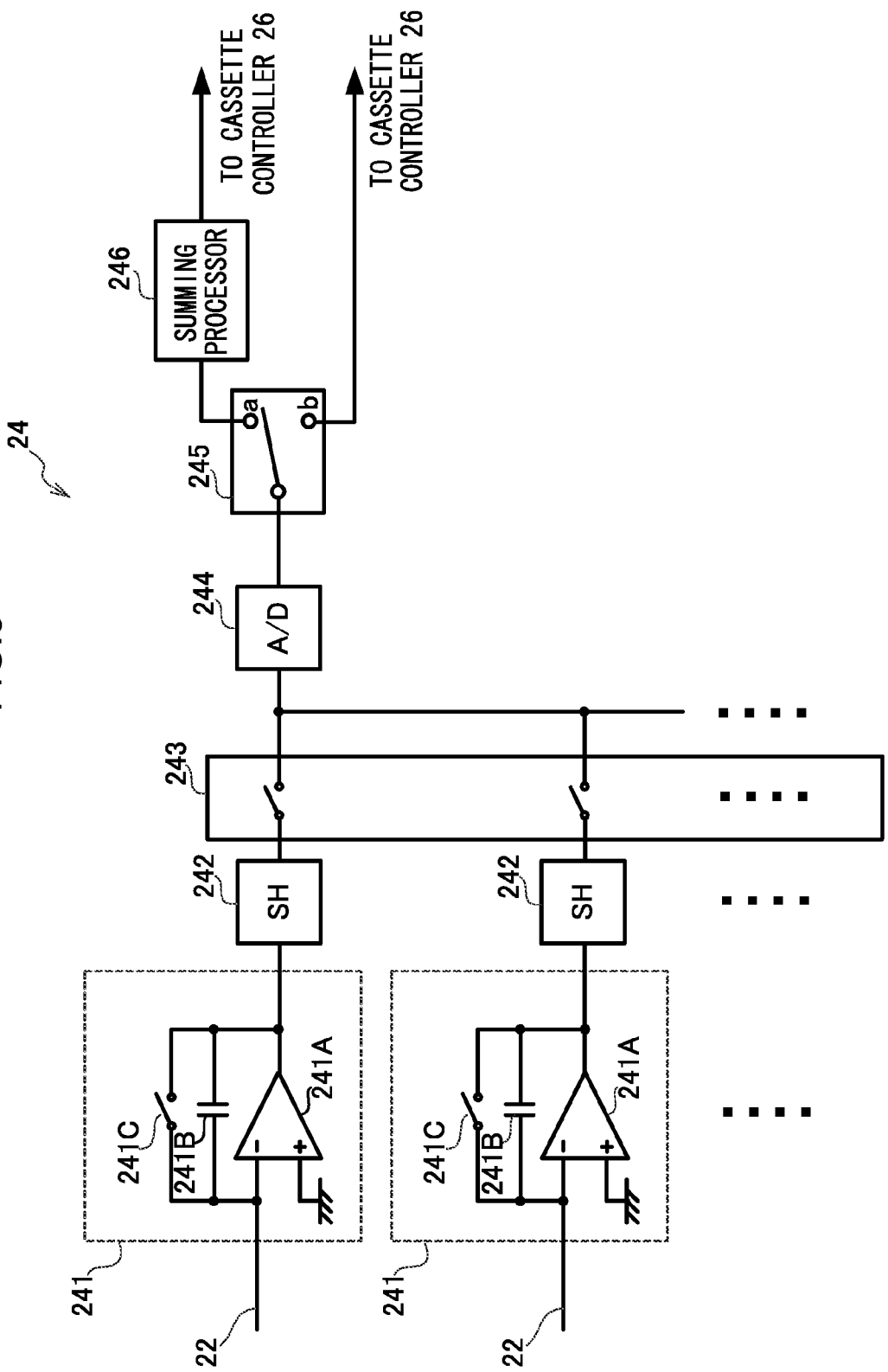

FIG.11

| IMAGING TARGET SITE | BLOCK SIZE (NUMBER OF PIXEL UNITS) |
|---|---|
| A | 1 |
| B | 2 |
| C | 4 |
| D | 9 |

FIG.23

| IMAGING TARGET SITE | THRESHOLD VALUE T PER SINGLE PIXEL UNIT |
|---|---|
| A | a |
| B | b |
| C | c |
| D | d |

501

RADIOGRAPHIC IMAGE CAPTURING DEVICE, METHOD FOR DETECTING RADIATION DOSES, AND COMPUTER READABLE STORAGE MEDIUM

CROSS-REFERENCE TO RELATED APPLICATIONS

This application is a continuation application of International Application No. PCT/JP2013/074433, filed Sep. 10, 2013, the disclosure of which is incorporated herein by reference in its entirety. Further, this application claims priority from Japanese Patent Application No. 2012-218258, filed Sep. 28, 2012, the disclosure of which is incorporated herein by reference in its entirety.

TECHNICAL FIELD

The present invention relates to a radiographic image capturing device that captures radiographic images expressing radiation that has passed through a subject, a computer readable storage medium storing a program for controlling the radiographic image capturing device, and a method for detecting radiation doses.

BACKGROUND ART

Recently, radiation detectors such as Flat Panel Detectors (FPDs) are being implemented, in which a radiation sensitive layer is disposed on a Thin Film Transistor (TFT) active matrix substrate, and with which radiation can be converted directly into digital data. Radiographic image capturing devices, such as electronic cassettes, that employ such radiation detectors and capture radiographic images expressing irradiated radiation are also being implemented. Methods used by radiation detectors to convert radiation into electrical signals include an indirect conversion method, in which radiation is first converted into light with a scintillator and then the converted light is converted into charges with a photodiode, and a direct conversion method in which radiation is directly converted into charges with a semiconductor layer including amorphous selenium and the like. There are various materials that can be used in the semiconductor layer for each method.

When employing a radiation detector to capture radiographic images, excellent image quality needs to be secured while minimizing the dose of radiation with which a subject is irradiated. In order to acquire radiographic images with excellent image quality, exposure control conditions need to be set for a radiation source such that exposure is with an appropriate dose of radiation according to the imaging target site. A radiographic image capture system provided with an Automatic Exposure Control (AEC) function is therefore proposed in which a radiation detector detects a cumulative radiation dose of radiation irradiated through the subject, and an irradiation stop timing of radiation from the radiation source is controlled based on the detection result. It is proposed that pixels that detect the dose of irradiated radiation are embedded in the radiation detector, separately to pixels that capture radiographic images in order to implement the Automatic Exposure Control (AEC).

For example, Japanese Patent Application Laid-Open (JP-A) No. 2012-15913 describes a radiographic image capturing device in which plural pixels, including pixels for radiographic image capture and pixels for radiation detection, are disposed in a matrix shape in a detection region for detecting radiation, and the irradiated dose of radiation is detected by detecting charges flowing in signal lines connected to the pixels for radiation detection.

SUMMARY OF INVENTION

In a radiation detector including plural radiation detection pixels such as that described in JP-A No. 2012-15913 above, if a defect occurs in a radiation detection pixel, an appropriate pixel value (signal value) cannot be obtained from the defective pixel. If Automatic Exposure Control (AEC) is performed based on the pixel value from the defective pixel, there is a possibility that radiation exposure cannot be stopped at the appropriate timing, and of irradiating the subject with an excessive radiation dose or an insufficient radiation dose, such that an appropriate radiographic image cannot be obtained. It is therefore preferable to employ only normal pixels, and not employ defective pixels, to detect the radiation dose if faults occur in the radiation detection pixels. In such cases, signals indicating the radiation dose cannot be obtained from defective pixels, and so great care is preferably taken to position the subject avoiding defective pixels, such that the subject is not disposed over defective pixels. However, it is sometimes difficult to position the subject to avoid defective pixels, depending on the position or size of the defective pixels.

In consideration of the above circumstances, there are provided a radiographic image capturing device, a method for detecting radiation doses, and a computer readable storage medium storing a program, in which a subject can be positioned easily, even in a case in which defects occur in radiation detection pixels that detect a dose of irradiated radiation.

According to an aspect of the present invention, there is provided a radiographic image capturing device which includes plural radiation dose detection pixels that respectively output signal values according to a dose of irradiated radiation, a determination unit that determines a presence or absence of defects, block-by-block, based on signal values of radiation dose detection pixels included in each of plural blocks, which are arranged such that the respective blocks include at least a portion of the plural radiation dose detection pixels, a block rearrangement unit that performs block rearrangement to change the arrangement of the plural blocks according to a determination result of the determination unit, and a detection unit that detects a dose of irradiated radiation based on signal values of each arranged block or of each rearranged block.

Namely, in the radiographic image capturing device according to the aspect of the present invention, the presence or absence of defects is determined for each arranged block using the determination unit, and the block rearrangement is performed by the block rearrangement unit in a case in which a defect has been determined to be present in any of the blocks. The detection unit detects the dose of irradiated radiation based on signal values of each arranged block or of each rearranged block.

In the radiographic image capturing device according to the aspect of the present invention, the block rearrangement unit may perform block rearrangement to change the arrangement of the plural blocks based on instruction input in a case in which the determination unit has determined that a defect is present in any of the plural blocks.

Namely, in a case in which the determination unit has determined that a defect is present in any of the plural blocks, the block rearrangement unit performs block rearrangement in a case in which instruction input to perform block rearrangement has been supplied.

In the radiographic image capturing device according to the aspect of the present invention, the block rearrangement may be performed by changing a block size of each of the plural blocks.

In the radiographic image capturing device according to the aspect of the present invention, the block rearrangement may be performed by moving inter-block boundaries defining each of the plural blocks, while maintaining a block size of each of the plural blocks.

The radiographic image capturing device according to the aspect of the present invention may be provided with a buffer region including plural radiation dose detection pixels that are capable of configuring a portion of any block rearranged by the block rearrangement unit. The buffer region is preferably provided at an outer periphery of a block group made up of the plural blocks.

The radiographic image capturing device according to the aspect of the present invention may be further provided with imaging pixels that output signal values according to a dose of irradiated radiation to capture radiographic images, and an identification unit that identifies an imaging target site for imaging by the imaging pixels. In such cases, each of the plural blocks preferably has a block size according to the imaging target site identified by the identification unit.

The radiographic image capturing device according to the aspect of the present invention may be further provided with a notification unit that notifies a placement of a defective block determined to have a defect by the determination unit, or a placement of a normal block other than the defective block.

In the radiographic image capturing device according to the aspect of the present invention, the detection unit may detect a dose of irradiated radiation based only on signal values of normal blocks other than defective blocks which have been determined to have a defect by the determination unit.

The radiographic image capturing device according to the aspect of the present invention may be further provided with a correction unit that corrects a signal value of a defective block which has been determined to have a defect by the determination unit, using a signal value of a normal block adjacent to the defective block.

According to another aspect of the present invention, there is provided a computer readable storage medium storing a program that is configured so as to cause a computer to function as the determination unit, the block rearrangement unit, and the detection unit of the above radiographic image capturing device.

According to another aspect of the present invention, there is provided a method for detecting radiation doses, which includes determining a presence or absence of defects, block-by-block, based on signal values of radiation dose detection pixels included in each of plural blocks, which are arranged such that the respective blocks include at least some out of plural radiation dose detection pixels that respectively output signal values according to a dose of irradiated radiation, performing block rearrangement to change the arrangement of the plural blocks in a case in which a defect is determined to be present in any of the plural blocks, and detecting a dose of irradiated radiation based on signal values of each arranged block or of each rearranged block.

According to the aspects of the present invention, block rearrangement is performed by the block rearrangement unit according to the determination results for the presence or absence of defects in the radiation dose detection pixels by the determination unit. The placement of defective blocks is accordingly changed, enabling easy positioning of an imaging subject avoiding defective blocks, even if defects occur in the radiation dose detection pixels.

BRIEF DESCRIPTION OF DRAWINGS

Embodiments of the present invention will be described in detail based on the following figures, wherein:

FIG. 8 is a block diagram illustrating a configuration of a signal processor.

FIG. 11 is a drawing illustrating a reference table according to an exemplary embodiment of the present invention, the reference table stored with correspondence relationships between imaging target sites and block arrangements.

FIG. 23 is a drawing illustrating a reference table according to an exemplary embodiment of the present invention, the reference table stored with correspondence relationships between imaging target sites and threshold values per single pixel unit.

DESCRIPTION OF EMBODIMENTS

Detailed explanation follows regarding an exemplary embodiment of the present invention, with reference to the drawings. Note that the following explanation illustrates an example in which the present invention is applied to a radiology information system, this being a system that performs overall management of information handled in a hospital radiology department.

Figure 1:
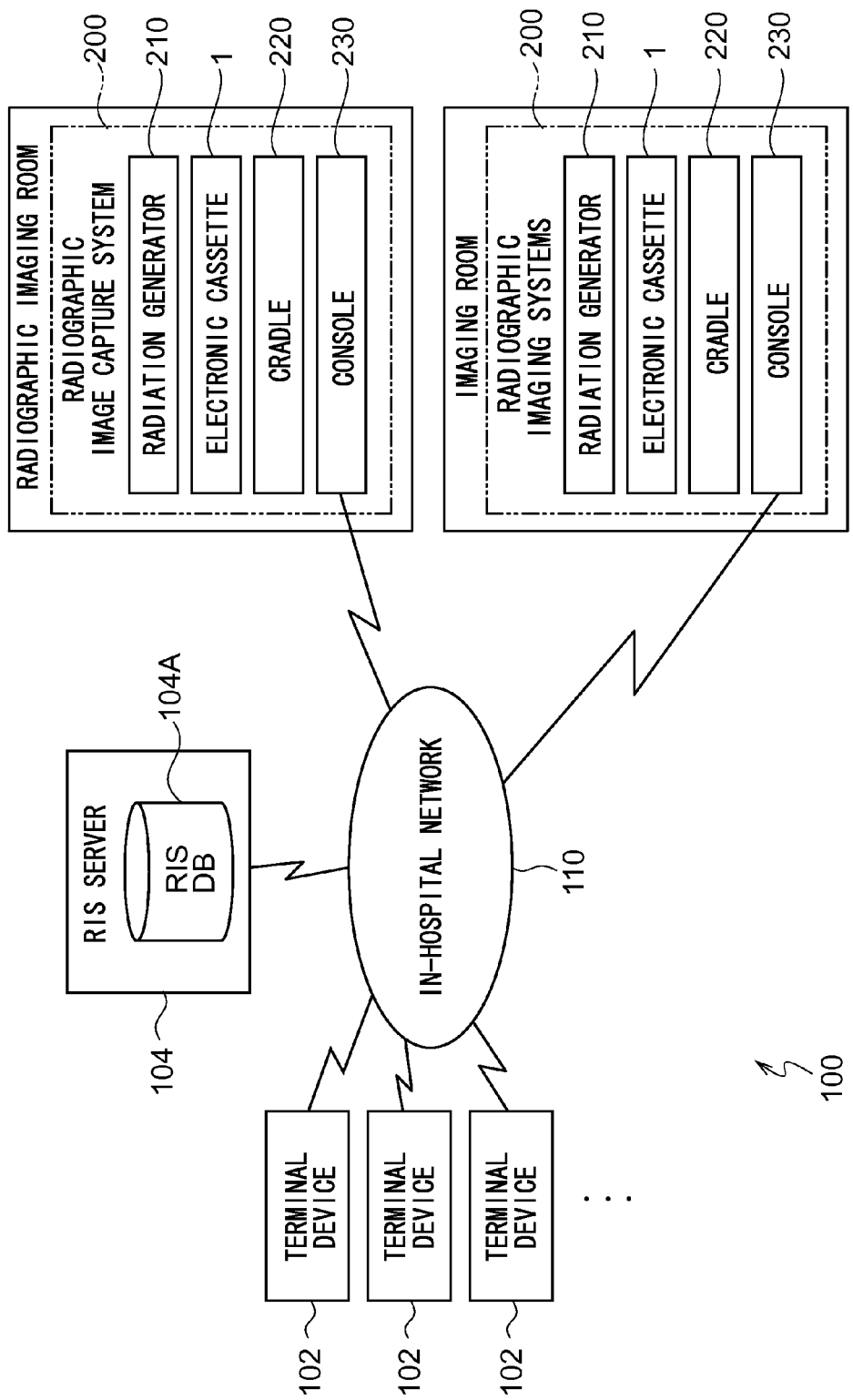
FIG. 1 is a block diagram illustrating a configuration of a radiology information system according to an exemplary embodiment of the present invention.

FIG. 1 illustrates a configuration of a radiology information system (referred to below as "RIS") 100 according to an exemplary embodiment of the present invention.

The RIS 100 is a system for managing information such as medical appointments and diagnostic records in a radiology department, and configures part of a hospital information system (referred to below as "HIS").

The RIS 100 includes plural imaging request terminal devices (referred to below as "terminal devices") 102, an RIS server 104, and radiographic image capture systems (referred to below as "imaging systems") 200. The imaging systems 200 are installed in individual radiographic imaging rooms (or operating rooms) in a hospital. The RIS 100 is configured by respectively connecting the terminal devices 102, the RIS server 104, and the imaging systems 200 to an in-hospital network 110 configured, for example, by a wired or wireless local area network (LAN). The RIS 100 configures part of the HIS provided in the same hospital, and an HIS server (not illustrated in the drawings) that manages the entire HIS is also connected to the in-hospital network 110.

The terminal devices 102 are used by doctors or radiologists to input and browse diagnostic information and facility reservations. Radiographic imaging requests and imaging reservations are also made using the terminal devices 102. Each of the terminal devices 102 includes a personal computer with a display device, and the terminal devices 102 are configured so as to intercommunicate with the RIS server 104 through the in-hospital network 110.

The RIS server 104 receives imaging requests from each of the terminal devices 102 and manages radiographic imaging schedules in the imaging systems 200. The RIS server 104 includes a database 104A.

The database 104A contains: information relating to patients, such as patient (imaging subject) attribute information (name, sex, date of birth, age, blood type, body weight, patient identification (ID), and the like), medical histories, consultation histories, radiographic images that have been captured in the past, and the like; information relating to electronic cassettes 1, described later, that are used in the imaging systems 200, such as electronic cassette 1 identification numbers (ID information), models, sizes, sensitivities, dates of first use, numbers of times used, and the like; and environment information indicating the environments in which radiographic images are captured using the electronic cassettes 1, namely the environments in which the electronic cassettes 1 are used (such as radiographic imaging rooms or operating rooms).

The imaging systems 200 are operated by doctors or radiologists to capture a radiographic image in response to an instruction from the RIS server 104. Each of the imaging systems 200 is provided with a radiation generator 210, an electronic cassette 1, a cradle 220, and a console 230. The radiation generator 210 includes a radiation source 211 (see also FIG. 2) that irradiates a patient (imaging subject) with a dose of X-rays or the like according to exposure conditions. The electronic cassette 1 has a built-in radiation detector 10 (see also FIG. 3) that absorbs radiation X that has passed through an imaging target site of a patient (imaging subject), generates charges, and creates image data expressing a radiographic image based on the amount of generated charges. The cradle 220 charges a battery that is built into the electronic cassette 1. The console 230 controls the electronic cassette 1 and the radiation generator 210.

The console 230 acquires various data contained in the database 104A from the RIS server 104, stores the data in a Hard Disk Drive (HDD) 236 (see FIG. 7), described later, and uses the data as needed to control the electronic cassette 1 and the radiation generator 210.

Figure 2:
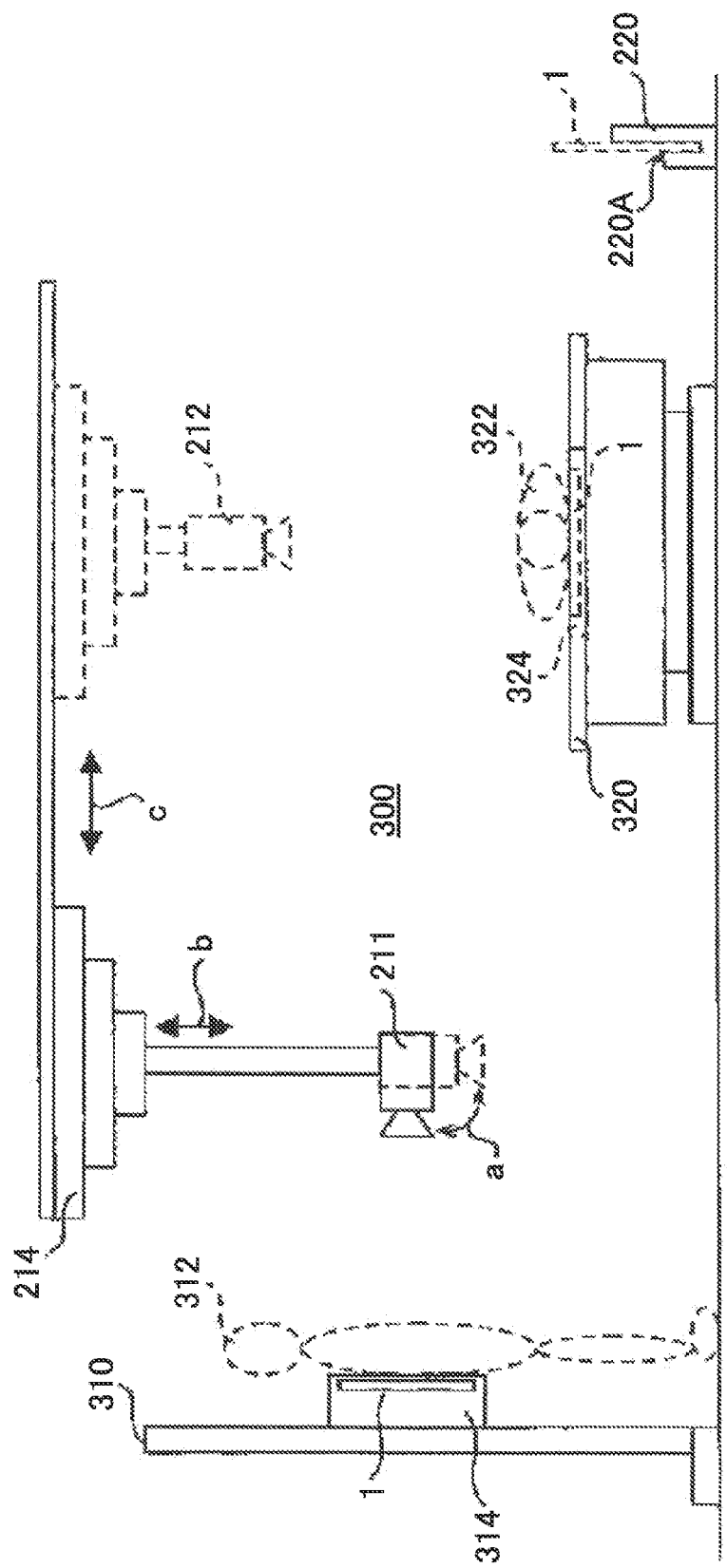
FIG. 2 is a side view illustrating an example of an installed state in a radiographic imaging room of respective devices of a radiographic image capture system according to an exemplary embodiment of the present invention.

FIG. 2 illustrates an example of an arrangement of each device of the imaging system 200 of an exemplary embodiment of the present invention in a radiographic imaging room 300.

As illustrated in FIG. 2, a standing position stand 310 used when performing radiographic imaging in a standing position, and a recumbent position table 320 used when performing radiographic imaging in a recumbent position, are installed in the radiographic imaging room 300. The space in front of the standing position stand 310 serves as a patient (imaging subject) imaging position 312 when performing radiographic imaging in the standing position. The space above the recumbent position table 320 serves as a patient (imaging subject) imaging position 322 when performing radiographic imaging in the recumbent position.

A holder 314 that holds the electronic cassette 1 is provided to the standing position stand 310. The electronic cassette 1 is held by the holder 314 when capturing a radiographic image in the standing position. Similarly, a holder 324 that holds the electronic cassette 1 is provided to the recumbent position table 320. The electronic cassette 1 is held by the holder 324 when capturing a radiographic image in the recumbent position.

The radiographic imaging room 300 is also provided with a supporting and moving mechanism 214 that supports the radiation source 211 such that the radiation source 211 is rotatable about a horizontal axis (the direction of arrow a in FIG. 2), is movable in the vertical direction (the direction of arrow b in FIG. 2), and is also movable in the horizontal direction (the direction of arrow c in FIG. 2). Radiographic imaging is accordingly possible in both the standing position and in the recumbent position using the single radiation source 211.

The cradle 220 includes a housing portion 220A that can house the electronic cassette 1. When the electronic cassette 1 is not in use, the electronic cassette 1 is housed in the housing portion 220A of the cradle 220, and the built-in battery of the electronic cassette 1 is charged.

In the imaging system 200, various data is transmitted and received by wireless communication between the radiation generator 210 and the console 230, and between the electronic cassette 1 and the console 230.

The electronic cassette 1 is not limited to being employed in a state held by the holder 314 of the standing position stand 310 or the holder 324 of the recumbent position table 320. Due to its portability the electronic cassette 1 may also be employed without being held by a holder, for example when imaging arm or leg regions.

Figure 3:
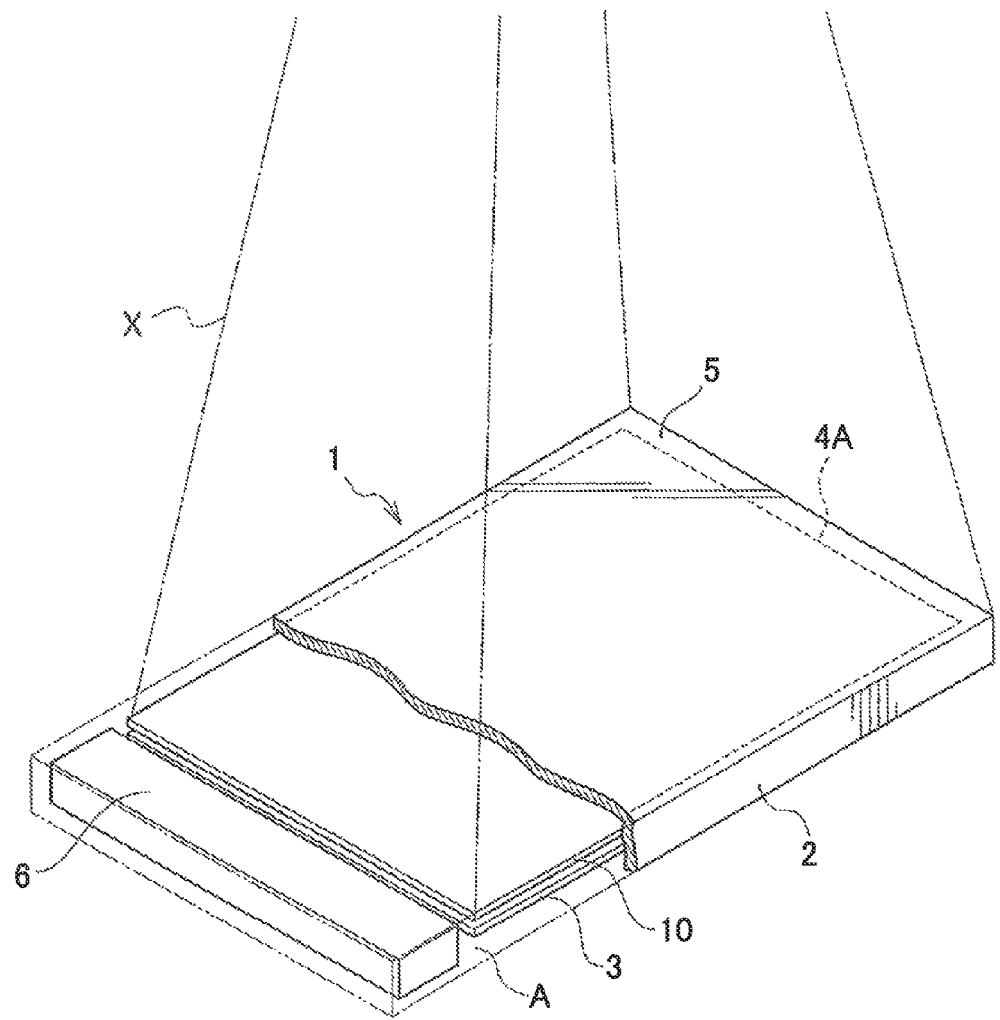
FIG. 3 is a perspective view illustrating a configuration of an electronic cassette according to an exemplary embodiment of the present invention.

Explanation follows regarding configuration of the electronic cassette 1 according to the present exemplary embodiment. FIG. 3 is a perspective view illustrating a configuration of the electronic cassette 1 serving as a radiographic image capturing device according to an exemplary embodiment of the present invention.

As illustrated in FIG. 3, the electronic cassette 1 is provided with a casing 2 that is formed from a material that allows radiation to pass through, and the electronic cassette 1 is configured with a waterproof sealed structure. When the electronic cassette 1 is used in an operating room or the like, there is the concern that blood or contaminants may adhere to the electronic cassette 1. Therefore, by configuring the electronic cassette 1 with a waterproof sealed structure and disinfecting the electronic cassette 1 as needed, the single electronic cassette 1 can be used repeatedly.

A space A that houses various components is formed inside the casing 2. The radiation detector 10, which detects the radiation X that has passed through the patient (imaging subject), and a lead plate 3, which absorbs backscattered rays of the radiation X, are disposed in this order inside the space A from an irradiated surface side of the casing 2 on which the radiation X is irradiated.

A region corresponding to the disposed position of the radiation detector 10 is configured as an imaging region 4A that is capable of detecting radiation. The imaging region 4A including a face of the casing 2 is configured as a top plate 5 of the electronic cassette 1. In the radiation detector 10 of the present exemplary embodiment, a TFT substrate 20, described later, is adhered to an inner face of the top plate 5. A case 6 that houses a cassette controller 26, described later, and a power source section 28 (see FIG. 7 for both) is placed at one end side of the interior of the casing 2 in a position that does not overlap with the radiation detector 10 (outside the range of the imaging region 4A).

The casing 2 is configured by carbon fiber, aluminum, magnesium, bionanofibers (cellulose microfibrils), or a composite material, for example, in order to make the overall electronic cassette 1 lightweight.

Figure 4:
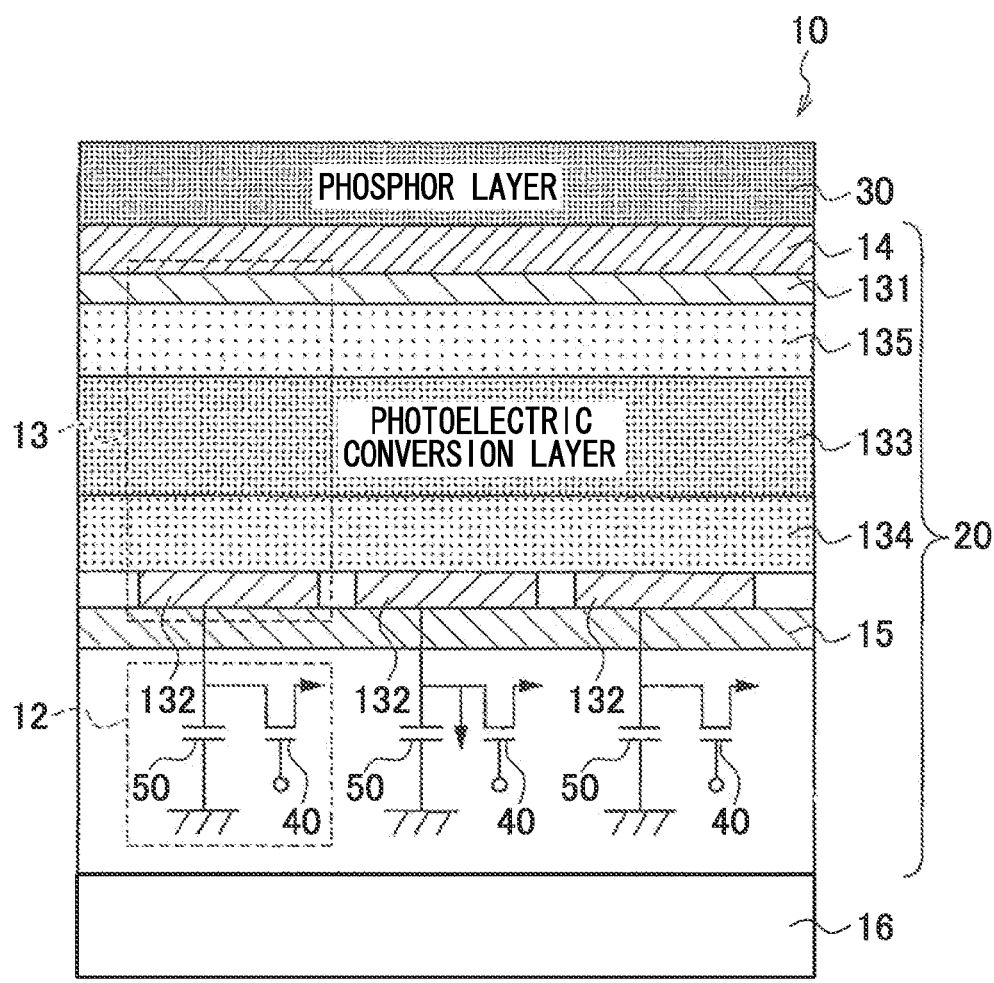
FIG. 4 is a cross-section illustrating a schematic configuration of a radiation detector according to an exemplary embodiment of the present invention.

Explanation follows regarding configuration of the inbuilt radiation detector 10 of the electronic cassette 1. FIG. 4 is a schematic cross-section of a layered structure of the radiation detector 10. The radiation detector 10 includes a TFT substrate, configured by forming signal output portions 12, sensor portions 13, and a transparent insulating film 14 in sequence on an insulating substrate 16, and a scintillator 30 that is a phosphor layer attached over the TFT substrate 20 employing, for example, a resin adhesive with low light absorbance.

The scintillator 30 is formed on the sensor portions 13 with the transparent insulating film 14 interposed therebetween. The scintillator 30 includes a phosphor that converts incident radiation into light and emits light. Namely, the scintillator 30 absorbs radiation that has passed through the patient (imaging subject) and emits light. The wavelength range of the light emitted by the scintillator 30 is preferably in the visible light range (a wavelength of from 360 nm to 830 nm), and more preferably includes a green wavelength region in order to enable monochrome imaging by the radiation detector 10. A phosphor including cesium iodide (CsI) is preferable as the phosphor employed for the scintillator 30 when X-rays are employed as the radiation, and CsI(Tl) (thallium doped cesium iodide) with an emission spectrum of from 420 nm to 700 nm when irradiated with X-rays is particularly preferable. Note that the emission peak wavelength in the visible light range of CsI(Tl) is 565 nm.

The sensor portions 13 each include an upper electrode 131, a lower electrode 132, and a photoelectric conversion layer 133 provided between the upper electrode 131 and the lower electrodes 132. The photoelectric conversion layer 133 is configured by an organic photoelectric conversion material that generates charges by absorbing the light emitted by the scintillator 30.

It is preferable for the upper electrode 131 to be configured by an electrically conductive material that is transparent at least with respect to the emission wavelength of the scintillator 30, since it is necessary to allow the light produced by the scintillator 30 to be made incident to the photoelectric conversion layer 133. Specifically, a transparent conducting oxide (TCO) with high transmittance with respect to visible light and a small resistance value is preferably employed. A thin metal film of Au or the like may also be employed for the upper electrode 131; however, since the resistance value thereof is liable to increase when trying to obtain a transmittance of 90% or more, TCO is more preferable. For example, ITO, IZO, AZO, FTO, $SnO_2$, $TiO_2$, $ZnO_2$, and the like are preferably employed for the upper electrode 131. ITO is most preferable from the perspectives of ease of processing, low resistance, and transparency. The upper electrode 131 may be configured as a single layer common to all the pixels, or may be divided per pixel.

The photoelectric conversion layer 133 includes an organic photoelectric conversion material, absorbs the light emitted from the scintillator 30, and generates charges according to the amount of absorbed light. The photoelectric conversion layer 133 containing the organic photoelectric conversion material accordingly has a sharp absorption spectrum in the visible range. There are virtually no electromagnetic waves other than the light emitted by the scintillator 30 absorbed by the photoelectric conversion layer 133. Accordingly, noise generated as a result of radiation such as X-rays being absorbed by the photoelectric conversion layer 133 can be effectively suppressed.

It is preferable for the absorption peak wavelength of the organic photoelectric conversion material configuring the photoelectric conversion layer 133 to be as close as possible to the emission peak wavelength of the scintillator 30, in order for the organic photoelectric conversion material to most efficiently absorb the light emitted by the scintillator 30. Ideally the absorption peak wavelength of the organic photoelectric conversion material and the emission peak wavelength of the scintillator 30 are the same as each other, but as long as the difference therebetween is small, the organic photoelectric conversion material can sufficiently absorb the light emitted from the scintillator 30. Specifically, it is preferable for the difference between the absorption peak wavelength of the organic photoelectric conversion material and the emission peak wavelength of the scintillator 30 with respect to radiation to be within 10 nm. The difference is more preferably within 5 nm. Examples of organic photoelectric conversion materials capable of satisfying this condition include quinacridone based organic compounds and phthalocyanine based organic compounds. For example, the absorption peak wavelength in the visible range of quinacridone is 560 nm. Therefore, if quinacridone is used as the organic photoelectric conversion material and CsI(Tl) is used as the material of the scintillator 30, it is possible to bring the difference between the peak wavelengths to within 5 nm, and the amount of charges generated in the photoelectric conversion layer 133 can be substantially maximized.

In order to suppress an increase in dark current, it is preferable to provide at least one out of an electron-blocking film 134 or a hole-blocking film 135, and it is more preferable to provide both. The electron-blocking film 134 may be provided between the lower electrodes 132 and the photoelectric conversion layer 133. The electron-blocking film 134 can suppress electrons from being injected from the lower electrodes 132 into the photoelectric conversion layer 133, increasing dark current, when a bias voltage has been applied between the lower electrodes 132 and the upper electrode 131. An electron-donating organic material may be used for the electron-blocking film 134. The hole-blocking film 135 may be provided between the photoelectric conversion layer 133 and the upper electrode 131. The hole-blocking film 135 can suppress holes from being injected from the upper electrode 131 into the photoelectric conversion layer 133, increasing dark current, when a bias voltage has been applied between the lower electrodes 132 and the upper electrode 131. An electron-accepting organic material may be used for the hole-blocking film 135.

Plural of the lower electrodes 132 are formed at intervals in a lattice pattern (matrix pattern), with one of the lower electrodes 132 corresponding to a single pixel. Each of the lower electrodes 132 is connected to a field-effect thin-film transistor (referred to below simply as a TFT) 40 and a capacitor 50 that configure the respective signal output portions 12. Note that an insulating film 15 is interposed between the signal output portions 12 and the lower electrodes 132, and the signal output portions 12 are formed on the insulating substrate 16. The insulating substrate 16 absorbs X-rays in the scintillator 30, and so is preferably a thin substrate (a substrate with a thickness in the region of several tens of μm) that has low absorbance of X-rays, is flexible, and has electrically insulating properties. Specifically, the insulating substrate 16 is preferably configured from a synthetic resin and aramid or bionanofibers, or a glass film that can be wound up into a roll (ultrathin glass), or the like.

The signal output portions 12 are provided to correspond to the lower electrodes 132, and each include the capacitor 50 that accumulates charge that has moved to the lower electrodes 132, and the TFT 40, serving as a switching element, that converts charges accumulated in the capacitor 50 into electrical signals and outputs the electrical signals.

The capacitor 50 is electrically connected to the corresponding lower electrode 132 by a conductive wire formed penetrating the insulating film 15. This enables charges captured in the lower electrode 132 to be moved to the capacitor 50. A gate electrode, a gate insulating film, and an active layer (channel layer), none of which are illustrated in the drawings, are layered in the TFT 40. A source electrode and a drain electrode are formed at a specific spacing from each other on the active layer.

In a case using what is referred to as a Penetration Side Sampling (PSS) method in which radiation imaging is performed by irradiating the radiation detector 10 with radiation from the side of the scintillator 30, light is emitted with higher intensity from the front face side of the scintillator 30. However, in a case using what is referred to as an Irradiation Side Sampling (ISS) method in which radiation imaging is performed by irradiating radiation from the TFT substrate 20 side, light is emitted with higher intensity from the side of the scintillator 30 face joined to the TFT substrate 20. In the radiation detector 10, the radiographic images captured are of higher resolution when an ISS method is employed than when a PSS method is employed since there is a shorter distance between the light emission position of the scintillator 30 and the TFT substrate 20.

Figure 5:
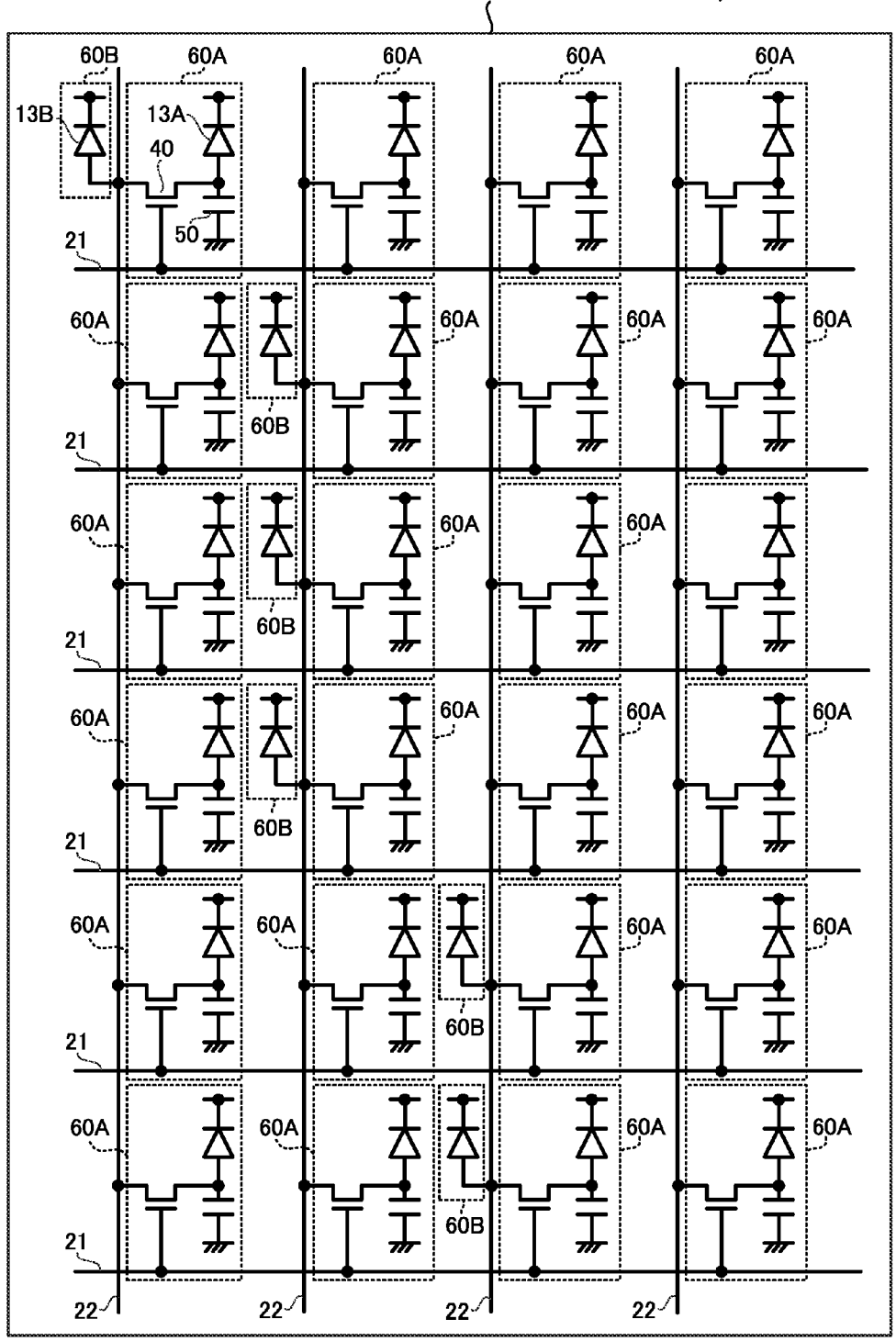
FIG. 5 is a drawing illustrating an electrical configuration of a radiation detector according to an exemplary embodiment of the present invention.

FIG. 5 illustrates an electrical configuration of the radiation detector 10 configuring the electronic cassette 1. The electronic cassette 1 according to the present exemplary embodiment not only has a function of capturing radiographic images, but also has a function of detecting a radiation dose that outputs a radiation dose detection signal indicating that a cumulative radiation dose with which the electronic cassette 1 has been irradiated through the patient (imaging subject) has reached a specific value. The radiographic imaging system 200 according to the present exemplary embodiment includes an Automatic Exposure Control function (referred to below as an AEC function) that controls a radiation irradiation stop timing of the radiation source 211 based on the radiation dose detection signal output from the electronic cassette 1. In order to implement the AEC function, in addition to plural imaging pixels 60A that capture radiation images, the radiation detector 10 also includes plural radiation dose detection pixels 60B that detect the cumulative radiation dose of the radiation with which the electronic cassette 1 has been irradiated through the imaging subject.

As illustrated in FIG. 5, the imaging pixels 60A include respective radiographic imaging sensors 13A, these being some of the sensor portions 13 configured including the photoelectric conversion layer 133 described above, the capacitors 50 that accumulate charges generated by the sensors 13A, and the TFTs 40 serving as switching elements that are switched ON during reading of the charges accumulated in the capacitors 50. The imaging pixels 60A are arrayed in a two-dimensional pattern so as to form rows and columns over the entire face of the TFT substrate 20.

The radiation detector 10 is provided with plural gate lines 21 that supply each of the TFTs 40 with gate signals to switch the respective TFTs 40 ON and OFF, the gate lines 21 extending in a specific direction (row direction) along the imaging pixel 60A array. The radiation detector 10 is also provided with plural signal lines 22 that in an ON state read the accumulated charges in the capacitors 50 through the TFTs 40, with the signal lines 22 extending in a direction (column direction) intersecting with the extension direction of the gate lines 21. Each of the imaging pixels 60A is provided corresponding to respective intersection portions between the gate lines 21 and the signal lines 22.

The radiation dose detection pixels 60B are configured by respective radiation dose detection sensors 13B, these being some of the sensor portions 13 configured including the photoelectric conversion layer 133 described above. The radiation dose detection sensors 13B are connected directly to the signal lines 22, and charges generated in the sensors 13B flow out unmodified into the signal lines 22. The radiation dose detection sensors 13B are distributed across the entire region of the TFT substrate 20. In the present exemplary embodiment, the number of the sensors 13B is set lower than the number of the radiographic imaging sensors 13A. In other words, the radiation dose detection pixels 60B are formed on the TFT substrate 20 at a lower density than the imaging pixels 60A. The radiographic imaging sensors 13A and the radiation dose detection sensors 13B are supplied with a bias voltage through bias lines, not illustrated in the drawings, and both the radiographic imaging sensors 13A and the radiation dose detection sensors 13B generate charges of an amount according to the dose of irradiated radiation. Note that the radiographic imaging sensors 13A and the radiation dose detection sensors 13B may be configured the same size as each other, or different sizes to each other.

Figure 6:
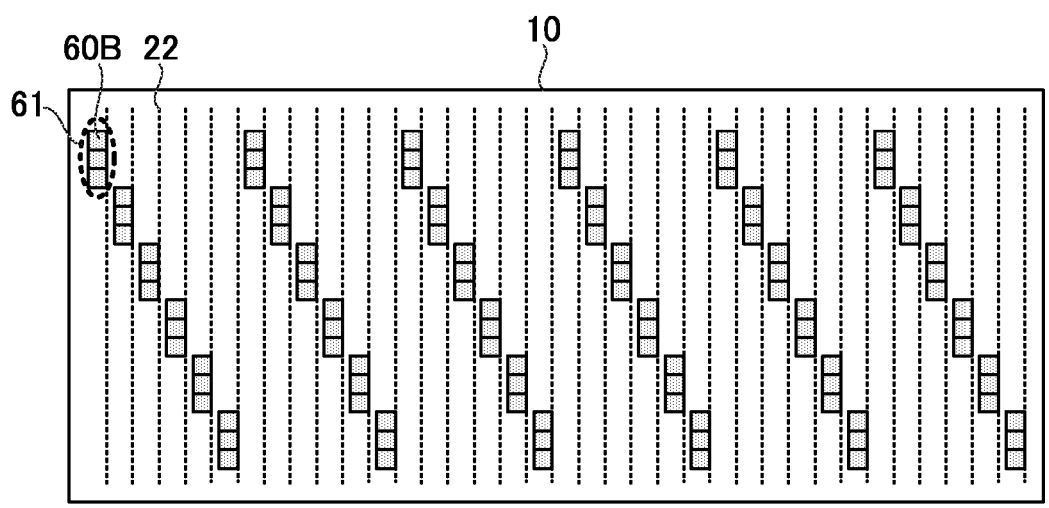
FIG. 6 is a plan view illustrating an example of a placement of radiation dose detection pixels in a radiation detector according to an exemplary embodiment of the present invention.

FIG. 6 is a plan view illustrating an example of a placement of the radiation dose detection pixels 60B in the radiation detector 10. Each of the signal lines 22 is connected to plural (3 in the example illustrated in FIG. 6) of the radiation dose detection pixels 60B in the extension direction of the signal lines 22, and the radiation dose detection pixels 60B are disposed with a substantially even distribution in the radiation detector 10. In the example illustrated in FIG. 6, three of the radiation dose detection pixels 60B (radiation dose detection sensors 13B) are connected to a single signal line 22, however the number of the radiation dose detection pixels 60B connected to a single signal line 22 may be varied as appropriate. The charges generated by the plural radiation dose detection pixels 60B connected to a single signal line 22 are summed together by merging in the corresponding signal line 22. Pixel units 61 are formed by the plural radiation dose detection pixels 60B connected to a single signal line 22, and blocks 62, described later, are configured from one, or from two or more, of the pixel units 61. Note that in the example illustrated in FIG. 6, each pixel unit 61 is configured by three of the radiation dose detection pixels 60B (sensors 13B).

Figure 7:
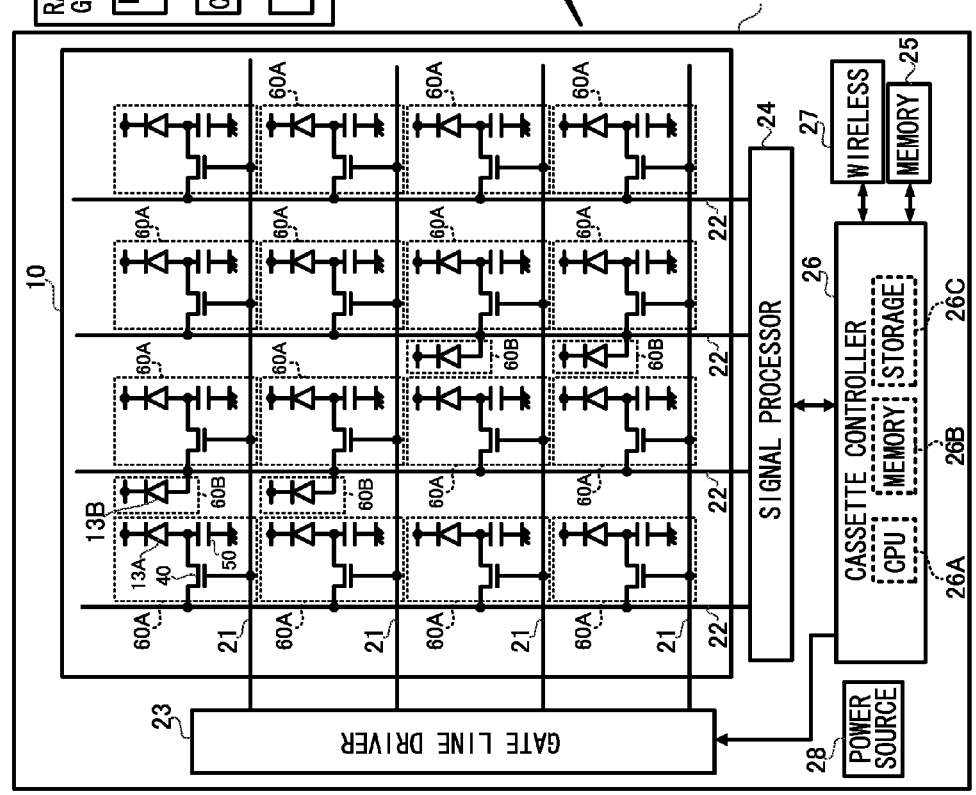
FIG. 7 is a drawing illustrating configuration of relevant portions of an electrical system of an imaging system according to an exemplary embodiment of the present invention.

FIG. 7 illustrates a configuration of relevant portions of an electrical system of the imaging system 200 according to the present exemplary embodiment. As illustrated in FIG. 7, a gate line driver 23 is disposed next to one of two adjacent sides of the inbuilt radiation detector 10 of the electronic cassette 1, and a signal processor 24 is disposed next to the other adjacent side. Each of the gate lines 21 is connected to the gate line driver 23, and each of the signal lines 22 is connected to the signal processor 24. The electronic cassette 1 includes an image memory 25, a cassette controller 26, a wireless communication section 27, and a power source section 28.

The TFTs 40 configuring the imaging pixels 60A are placed in an ON state in row units by gate signals supplied from the gate line driver 23 through the gate lines 21. The charges generated in the radiographic imaging sensors 13A and accumulated in the capacitors 50 are read into the respective signal lines 22 as electrical signals, and transmitted to the signal processor 24, by placing the TFTs 40 in the ON state. The charges generated in the radiation dose detection sensors 13B configuring the radiation dose detection pixels 60B flow out into the signal lines 22 and are sequentially supplied to the signal processor 24, irrespective of the gate signals from the gate line driver 23.

FIG. 8 illustrates a configuration of the signal processor 24. The signal processor 24 includes plural charge amplifiers 241 respectively connected to each of the signal lines 22. Each of the charge amplifiers 241 includes an operational amplifier (operational amplifier circuit) 241A with the inverting terminal connected to the corresponding signal line 22, and the non-inverting terminal connected to a ground potential, a capacitor 241B with one terminal connected to the inverting terminal of the operational amplifier 241A and the other terminal connected to the output terminal of the operational amplifier 241A, and a reset switch 241C connected in parallel to the capacitor 241B.

The charges generated in each of the respective imaging pixels 60A or radiation dose detection pixels 60B are accumulated in the capacitors 241B of the charge amplifiers 241 through the signal lines 22. The charge amplifiers 241 generate electrical signals with a signal level according to the amount of charge accumulated in the capacitor 241B, and these electrical signals are supplied to a sample-and-hold circuit 242. The charges accumulated in the capacitors 241B are released by placing the reset switches 241C in an ON state in response to a control signal supplied from the cassette controller 26, thereby resetting the electrical signals output from the charge amplifiers 241.

The sample-and-hold circuits 242 sample and hold signal levels of the output signals from the charge amplifier 241 in response to a control signal supplied from the cassette controller 26, and supply the signal level of the held signals to a multiplexer 243.

The multiplexer 243 selects and outputs the signal levels held in the sample-and-hold circuits 242 in sequence in response to a control signal supplied from the cassette controller 26. Namely, the multiplexer 243 converts electrical signals from the sample-and-hold circuits 242 to serial data, and supplies the serial data to an analogue/digital converter (A/D converter) 244 in sequence.

The A/D converter 244 converts the signal levels of electrical signals sequentially supplied from the multiplexer 243 into digital signals. Namely, the A/D converter 244 outputs pixel values (signal values) of the imaging pixels 60A or the radiation dose detection pixels 60B as digital signals.

A switch portion 245 is a switch that selects whether to transmit the digital signals from the A/D converter 244 to the cassette controller 26 via a summing processor 246, or whether to transmit the digital signals directly to the cassette controller 26, in response to a control signal supplied from the cassette controller 26. The digital signals from the A/D converter 244 are supplied to the summing processor 246 by connecting the switch of the switch portion 245 to a contact point a side, and the digital signals from the A/D converter 244 are supplied to the cassette controller 26 by connecting the switch to the contact point b side.

The summing processor 246 sums the digitalized pixel values (signal values) supplied from the A/D converter 244 through the switch portion 245 based on block arrangement data, described later, supplied from the cassette controller 26. As described later, in the electronic cassette 1 according to the present exemplary embodiment, blocks 62 each which forms of plural radiation dose detection pixels 60B are arranged. The summing processor 246 performs processing block-by-block to sum the pixel values of the radiation dose detection pixels 60B belonging to the same block, and supplies the obtained value to the cassette controller 26 as a pixel value for the corresponding block. Note that in the present exemplary embodiment, the pixel values for each block are acquired by summing the digitalized pixel values supplied from the A/D converter 244, however configuration may be made such that analogue signals supplied from the multiplexer 243 are collected block-by-block, and the pixel values acquired block-by-block as analogue data, after which the analogue data is digitalized.

The image memory 25 has sufficient memory capacity to store a specific number of frames of image data. Each time radiographic image capture is performed, the captured image data is sequentially stored in the image memory 25. The image memory 25 is connected to the cassette controller 26.

The cassette controller 26 performs overall control of operation of the electronic cassette 1. The cassette controller 26 is configured including a microcomputer, and is provided with a Central Processing Unit (CPU) 26A, memory 26B including Read Only Memory (ROM) and Random Access Memory (RAM), and a non-volatile storage section 26C configured by flash memory or the like. The cassette controller 26 is connected to the wireless communication section 27.

The wireless communication section 27 conforms to a wireless LAN standard, as typified by, for example, the Institute of Electrical and Electronics Engineers (IEEE) standards 802.11 a/b/g, and controls transmission of various data to and from an external device by wireless communication. The cassette controller 26 is capable of wireless communication with an external device such as the console 230 that performs control relating to radiographic image capture through the wireless communication section 27, such that it is possible to transmit and receive various data to and from the console 230, for example.

The electronic cassette 1 is provided with the power source section 28. The respective circuits and respective elements of the electronic cassette 1 (the microcomputer functioning as the gate line driver 23, the signal processor 24, the image memory 25, the wireless communication section 27, and the cassette controller 26) operate using power supplied from the power source section 28. In order not to impair the portability of the electronic cassette 1, the power source section 28 is configured by an inbuilt battery (a rechargeable secondary battery). The charged battery supplies power to the respective circuits and elements. Note that FIG. 7 omits illustration of wiring connecting the respective circuits and elements to the power source section 28.

The console 230 is configured by a server computer, and includes a display 231 that displays, for example, operation menus and captured radiographic images, and an operation panel 232 that is configured including plural keys and input with various data and operation instructions.

The console 230 according to the present exemplary embodiment is provided with a CPU 233 that controls the operation of the device as a whole, ROM 234 that is stored in advance with various programs and the like, including a control program, RAM 235 that temporarily stores various data, an HDD 236 that stores and holds various data, a display driver 237 that controls display of various information on the display 231, and an operation input detection section 238 that detects an operational state to the operation panel 232. The console 230 transmits and receives various data such as the exposure conditions, described later, to and from the radiation generator 210 by wireless communication, and is provided with a wireless communication section 239 that performs transmission and reception of various data such as image data to and from the electronic cassette 1.

The CPU 233, the ROM 234, the RAM 235, the HDD 236, the display driver 237, the operation input detection section 238, and the wireless communication section 239 are mutually connected together through a system bus, BUS. The CPU 233 can thereby access the ROM 234, the RAM 235, and the HDD 236, can control the display through the display driver 237 of various information on the display 231, and can control the transmission and reception of various data to and from the radiation generator 210 and the electronic cassette 1 through the wireless communication section 239. Through the operation input detection section 238, the CPU 233 can also ascertain an operational state of the operation panel 232 by a user.

The radiation generator 210 is provided with the radiation source 211, a wireless communication section 213 that transmits and receives various data such as the exposure conditions to and from the console 230, and a controller 212 that controls the radiation source 211 based on received exposure conditions. The controller 212 is also configured including a microcomputer, and stores received exposure conditions and the like. The exposure conditions received from the console 230 include data relating to tube voltage and tube current. The controller 212 emits radiation from the radiation source 211 based on the received exposure conditions.

Block Arrangement Processing

Figure 9A:
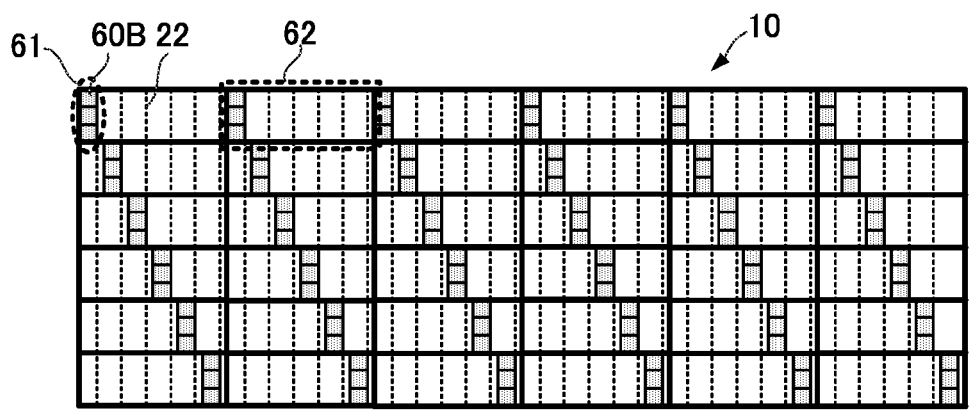
FIG. 9A is a drawing illustrating an example of a block arrangement of radiation dose detection pixels in an electronic cassette according to an exemplary embodiment of the present invention.
Figure 9B:
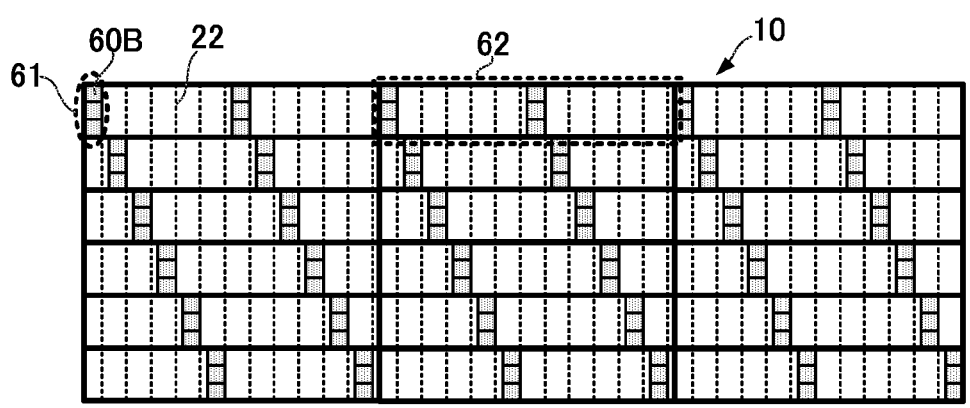
FIG. 9B is a drawing illustrating an example of a block arrangement of radiation dose detection pixels in an electronic cassette according to an exemplary embodiment of the present invention.
Figure 9C:
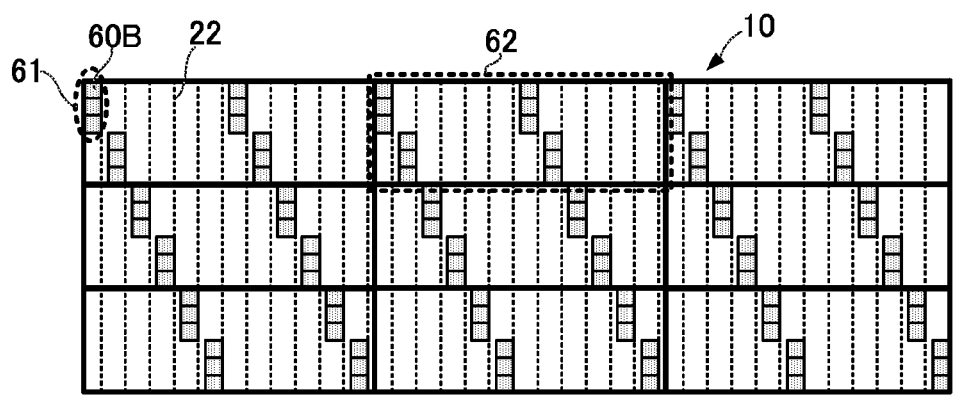
FIG. 9C is a drawing illustrating an example of a block arrangement of radiation dose detection pixels in an electronic cassette according to an exemplary embodiment of the present invention.
Figure 9D:
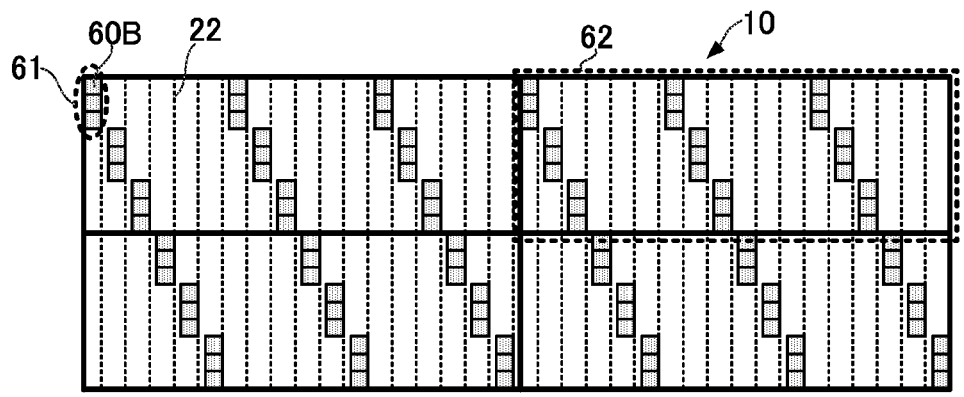
FIG. 9D is a drawing illustrating an example of a block arrangement of radiation dose detection pixels in an electronic cassette according to an exemplary embodiment of the present invention.

Explanation follows regarding block arrangement processing of the pixel blocks configured from plural of the radiation dose detection pixels 60B that is executed by the electronic cassette 1 according to the present exemplary embodiment. FIG. 9A to FIG. 9D illustrate configurations of block arrangement of the radiation dose detection pixels 60B provided to the radiation detector 10. The electronic cassette 1 performs block arrangement using minimum units of the pixel units 61 respectively configured by plural (three in the examples illustrated in FIG. 9A to FIG. 9D) radiation dose detection pixels 60B connected to a single signal line 22, and performs radiation dose detection of the radiation irradiated onto the electronic cassette 1 by treating each block as a single pixel (sensor). FIG. 9A illustrates a block arrangement in which a single pixel unit 61 is included in each block 62. Namely, plural blocks 62, each of which includes three of the radiation dose detection pixels 60B, are arranged. FIG. 9B illustrates a block arrangement in which two of the pixel units 61 are included in each block 62. Namely, plural blocks 62, each of which includes six of the radiation dose detection pixels 60B, are arranged. FIG. 9C illustrates a block arrangement in which four of the pixel units 61 are included in each block 62. Namely, plural blocks 62, each of which includes twelve of the radiation dose detection pixels 60B, are arranged. FIG. 9D illustrates a block arrangement in which nine of the pixel units 61 are included in each block 62. Namely, plural blocks 62, each of which includes 27 of the radiation dose detection pixels 60B, are arranged. In the electronic cassette 1, the plural blocks 62, each of which includes one or plural of the pixel units 61, are arranged, in which the number of pixel units 61 (namely the number of radiation dose detection pixels 60B) included in a single block 62 may be varied as appropriate. In other words, in the radiation detector 10 according to the present exemplary embodiment each of the plural blocks 62 has a changeable block size.

Before the electronic cassette 1 executes block arrangement processing, an imaging technician inputs radiographic image capture condition settings using the operation panel 232 of the console 230. Namely, the CPU 233 of the console 230 controls the display driver 237 to display a specific initial data input screen on the display 231. The initial data input screen displays messages prompting input of the name of the patient (imaging subject) for radiographic image capture, imaging target site, posture during imaging, and tube voltage and tube current during radiation exposure, and displays input regions for this data. When the initial data input screen has been displayed by the display 231, the imaging technician then inputs the name of the patient (imaging subject) for image capture, the imaging target site, the posture for image capture, and the exposure conditions to each corresponding input region using the operation panel 112. When the imaging technician has completed the input operation of the initial data of the initial data input screen, the CPU 233 then transmits the initial data input to the initial data input screen to the electronic cassette 1 through the wireless communication section 119.

Figure 10:
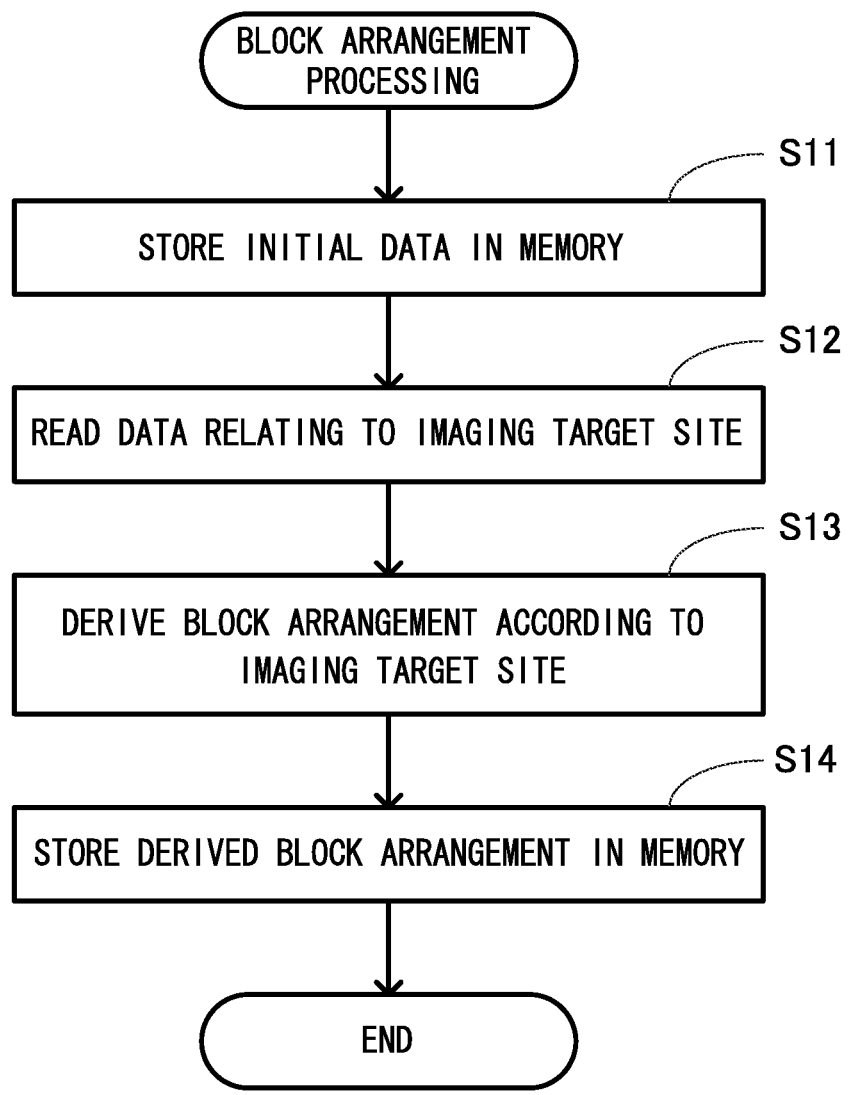
FIG. 10 is a flowchart illustrating a flow of processing in a block arrangement processing program according to an exemplary embodiment of the present invention.

On receipt of the above initial data from the console 230, the electronic cassette 1 executes the block arrangement processing. FIG. 10 is a flowchart illustrating a flow of processing in a block arrangement processing program executed by the CPU 26A of the cassette controller 26 of the electronic cassette 1 on receipt of the above initial data. The program is stored in advance in a specific region of the storage section 26C of the cassette controller 26.

At step S11, the CPU 26A of the cassette controller 26 retains the initial data received from the console 230 in the memory 26B, and at step S12, data included in the initial data relating to the imaging target site is read from the memory 26B.

At step S13, the CPU 26A derives the block arrangement for the radiation dose detection pixels 60B (the block size of each block) corresponding to the imaging target site indicated by the data read from the memory 26B at step S12. The cassette controller 26, for example, refers to a reference table 500, such as that illustrated in FIG. 11, stored in advance in the storage section 26C, to derive the block arrangement (block size) corresponding to the imaging target site. The reference table 500 includes block arrangements (block sizes) associated with each imaging target site. For example, sites that are comparatively small in size, such as fingers, are associated with comparatively small block sizes, and sites that are comparatively large in size, such as the chest area, are associated with comparatively large block sizes.

At step S14, the CPU 26A retains the block arrangement derived at step S13 in the memory 26B, and the present routine is ended. Deriving and storing the block arrangement (block size) according to the imaging target site so as to be appropriate to the size of the imaging target site, for example, enables radiation dose detection of the radiation irradiated during radiographic image capture to be performed at a spatial resolution according to the size of the imaging target site.

Block Selection Processing

Note that in order to perform appropriate Automatic Exposure Control (AEC), the range of valid blocks employed in detection of the cumulative radiation dose in the radiation detector 10 (referred to below as valid blocks) is preferably set so as to substantially match a region where the imaging subject covers the radiation detector 10 (referred to below as the imaging subject region). In other words, blocks positioned in what is known as a directly irradiated region, where the radiation detector 10 is directly irradiated by radiation that has not passed through the imaging subject, are preferably treated as invalid blocks that are not employed in radiation dose detection (referred to below as invalid blocks). The electronic cassette 1 according to the present exemplary embodiment includes a block selection function, in which the radiation dose detection pixels 60B are employed to capture a simple radiographic image of the imaging subject and identify an imaging subject region, and blocks positioned directly below the identified imaging subject region are set as the valid blocks employed in radiation dose detection, and other blocks are set as invalid blocks that are not employed in radiation dose detection.

Figure 12:
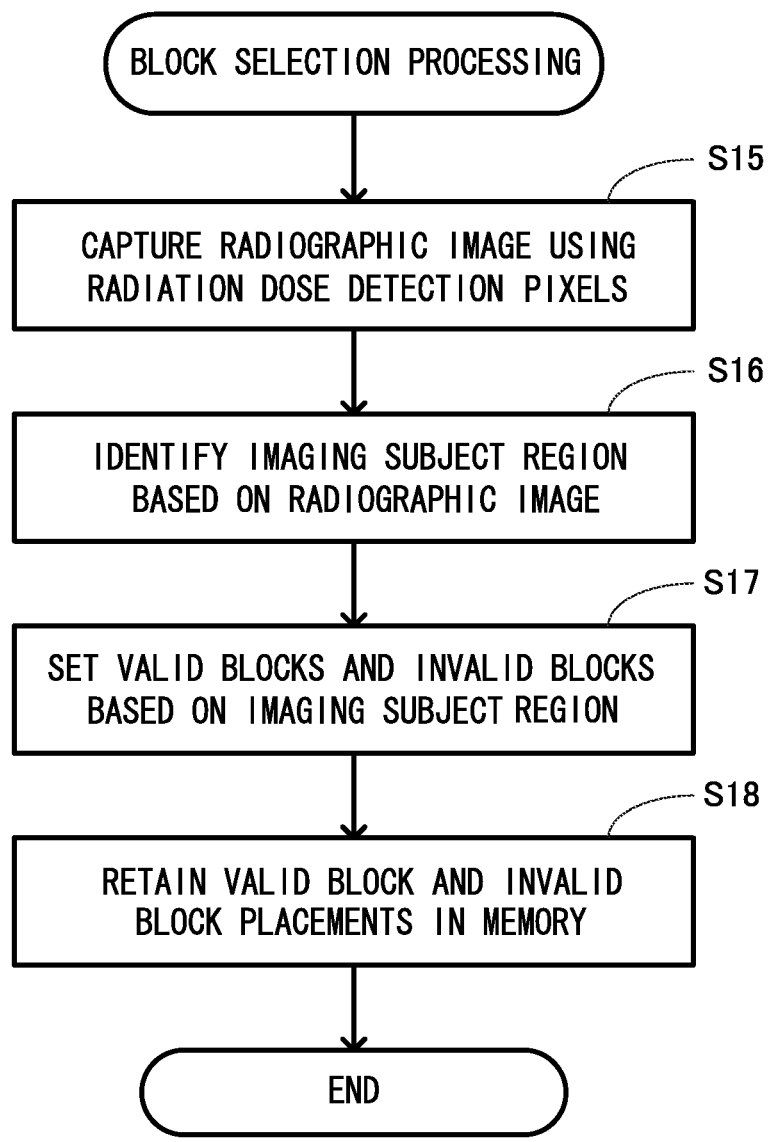
FIG. 12 is a flowchart illustrating a flow of processing in a block selection processing program according to an exemplary embodiment of the present invention.

FIG. 12 is a flowchart illustrating a flow of processing in a block selection processing program executed by the electronic cassette 1 to implement the block selection function described above. The program is stored in advance in a specific region of the storage section 26C of the cassette controller 26. The program is executed at a specific timing during diagnostic radiographic image capture by the imaging pixels 60A. Note that the block arrangement processing described above is executed, and the block arrangement derived according to the imaging target site is stored in the memory 26B, prior to executing the block selection processing program.

At step S15, the CPU 26A of the cassette controller 26 employs the radiation dose detection pixels 60B to capture a radiographic image of the imaging subject. Here, the CPU 26A supplies a control signal to the switch portion 245 to connect the switch to the contact point b side. The CPU 26A also supplies a control signal to the gate line driver 23 to drive each of the TFTs 40 of the imaging pixels 60A to an OFF state. The radiation emitted from the radiation source 211 then irradiates the electronic cassette 1 through the imaging subject. The charges generated in the sensors 13A of each of the imaging pixels 60A are accumulated in the capacitors 50. However, charges arising in the sensors 13B of each of the radiation dose detection pixels 60B are supplied to the signal processor 24 through the respective signal lines 22. Note that charges from the plural radiation dose detection pixels 60B configuring the pixel units 61 connected to the same signal line 22 merge in the signal line 22 and are supplied to the signal processor 24. In the signal processor 24, the pixel values (signal values) of each of the pixel units 61 supplied through the respective signal lines 22 are converted into digital values and supplied to the cassette controller 26. The cassette controller 26 generates a radiographic image based on the digitalized pixel values of each of the pixel units 61, and retains the radiographic image in the image memory 25.

At step S16, the CPU 26A reads and analyzes the radiographic image held in the image memory 25, and identifies the imaging subject region that is the region where radiation irradiates the radiation detector 10 through the imaging subject. Note that in the present exemplary embodiment, the number of the radiation dose detection pixels 60B is smaller than the number of the imaging pixels 60A, and the pixel units 61 function as a single pixel, and so image capture by the radiation dose detection pixels 60B obtains a comparatively low resolution image. However, a sufficient number of pixels are secured for the radiation dose detection pixels 60B to identify the imaging subject region.

At step S17, among the blocks arranged in the block arrangement processing described above (see FIG. 10), for example, the CPU 26A sets blocks of which at least a portion overlaps with the imaging subject region identified at step S16 as the valid blocks employed in radiation dose detection, and sets blocks that do not include an overlapping portion with the imaging subject region as the invalid blocks not employed in radiation dose detection. Namely, blocks that are irradiated with radiation through the imaging subject are set as the valid blocks, and other blocks are set as the invalid blocks. Note that configuration may be made such that blocks that completely overlap with the imaging subject region, or blocks of which more than half of the block overlaps with the imaging subject region, are set as the valid blocks.

At step S18, the CPU 26A retains in the memory 26B placement data indicating the placement of the blocks respectively set as valid blocks and invalid blocks at step S17, and the present routine is ended.

Radiation Dose Detection Processing

Explanation follows regarding first radiation dose detection processing in which the radiation dose detection pixels 60B arranged into blocks in the block arrangement processing described above are employed to detect a cumulative radiation dose of radiation irradiated onto the electronic cassette 1.

Figure 13:
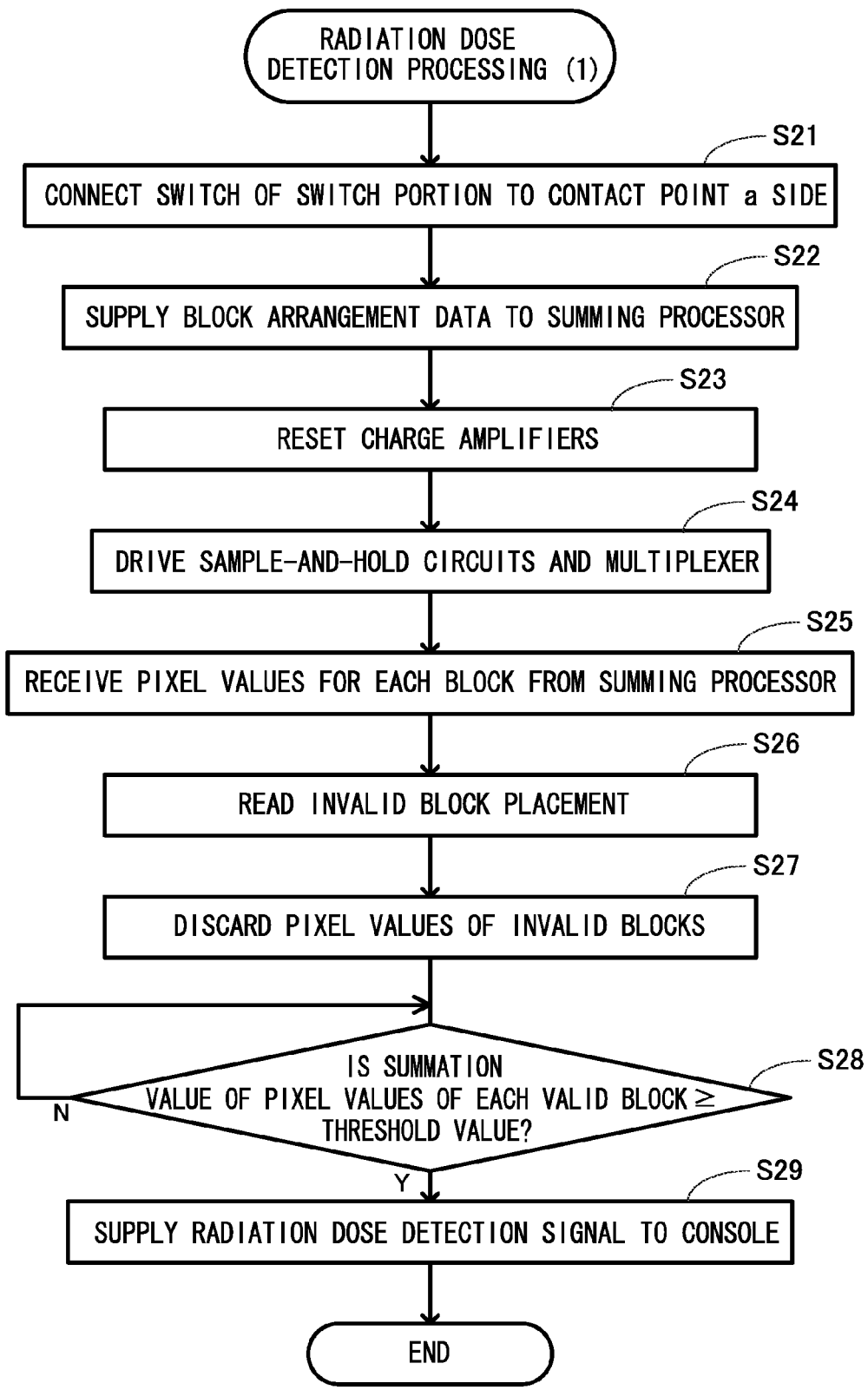
FIG. 13 is a flowchart illustrating a flow of processing in a first radiation dose detection program according to an exemplary embodiment of the present invention.

FIG. 13 is a flowchart illustrating a flow of processing in a first radiation dose detection processing program executed by the CPU 26A of the cassette controller 26 of the electronic cassette 1. The program is stored in advance in a specific region of the storage section 26C of the cassette controller 26. The program is executed at a specific timing during diagnostic radiographic image capture using the imaging pixels 60A.

At step S21, the CPU 26A of the cassette controller 26 supplies a control signal to the switch portion 245 of the signal processor 24. On receipt of this signal, the switch portion 245 connects the switch to the contact point a side.

At step S22, the CPU 26A supplies the summing processor 246 of the signal processor 24 with block arrangement data indicating the content of the block arrangement derived in the block arrangement processing described above (see FIG. 10).

At step S23, the CPU 26A supplies a control signal to the charge amplifiers 241 of the signal processor 24. On receipt of this control signal, the charge amplifiers 241 place the reset switches 241C in an ON state, thereby resetting the charge amplifiers 241. On completion of charge amplifier 241 reset, the reset switches 241C are driven to an OFF state.

At step S24, the CPU 26A supplies control signals to the sample-and-hold circuits 242 and the multiplexer 243, driving the sample-and-hold circuits 242 and the multiplexer 243 in synchronization with each other. Each of the imaging pixels 60A and each of the radiation dose detection pixels 60B then generate charges on irradiation of the electronic cassette 1 with radiation. All of the TFTs 40 are in the OFF state over the duration in which the electronic cassette 1 is irradiated with radiation, and the charges generated in the imaging pixels 60A accumulate in the capacitors 50. However, the charges generated in the radiation dose detection pixels 60B are input into the charge amplifiers 241 connected to the respective signal lines through the respective signal lines 22. Note that charges from the plural radiation dose detection pixels 60B configuring pixel units 61 connected to the same signal line 22 are merged in the signal line 22 and supplied to the signal processor 24.

Each of the charge amplifiers 241 outputs an output signal according to the amount of charges supplied through the signal line 22. The sample-and-hold circuits 242 sample the output signals of the charge amplifiers 241 at a sampling cycle according to a control signal supplied from the CPU 26A of the cassette controller 26. The multiplexer 243 supplies the outputs of the respective sample-and-hold circuits 242 to the A/D converter 244 in sequence, synchronized with the sampling cycle. The A/D converter 244 converts the analogue signals sequentially supplied from the multiplexer 243 into digital signals. Namely, the A/D converter 244 sequentially outputs sampled values of the outputs of the respective charge amplifiers 241 as digital values. The output values of the A/D converter 244 are sequentially supplied to the summing processor 246 through the switch portion 245.

The summing processor 246 ascertains the block arrangement of the radiation dose detection pixels 60B based on the block arrangement data supplied from the CPU 26A at step S22, and, for each block, performs processing to sum together the output values from the A/D converter 244 belonging to the same block. The summing processor 246 supplies the summation values computed for each block to the CPU 26A as dose data (a pixel value (signal value)) indicating the cumulative radiation dose detected for that block.

At step S25, the CPU 26A receives the dose data (pixel values) for each block supplied from the summing processor 246.

At step S26, the CPU 26A of the cassette controller 26 identifies the placement of the invalid blocks by reading the placement data indicating the placement of the invalid blocks not employed in radiation dose detection stored in the memory 26B at step S15 of the block arrangement processing described above (see FIG. 10).

At step S27, the CPU 26A excludes or discards the dose data (pixel values) corresponding to the invalid blocks identified at step S26 out of the dose data (pixel values) of each block supplied from the summing processor 246 at step S25.

At step S28, the CPU 26A determines whether or not a summation value (cumulative value) of the dose data (pixel values) of each of the remaining valid blocks is a specific threshold value or above. The electronic cassette 1 uses this determination to detect that the cumulative radiation dose of radiation irradiated onto the radiation detector 10 through the imaging subject has reached the specific value. Processing transitions to step S29 in a case in which the CPU 26A determines that the summation value (cumulative value) of the dose data (pixel values) from each of the valid blocks has reached the specific threshold value or above.

At step S29, the CPU 26A generates a radiation dose detection signal indicating that the cumulative radiation dose with which the electronic cassette 1 has been irradiated has reached the specific value or above, and supplies the radiation dose detection signal to the console 230. The present routine is then ended.

On receipt of the radiation dose detection signal, the CPU 233 of the console 230 supplies the radiation generator 210 with a control signal instructing radiation irradiation to be stopped. On receipt of this control signal, the radiation generator 210 stops radiation irradiation. Automatic Exposure Control (AEC), which controls the timing at which radiation irradiation by the radiation source 211 is stopped, is realized by detecting the cumulative radiation dose of radiation irradiated onto the electronic cassette 1 using the radiation dose detection pixels 60B in arranged blocks in this manner. Moreover, due to employing a block arrangement corresponding to the imaging target site, the electronic cassette 1 according to the present exemplary embodiment enables the cumulative radiation dose to be detected at a spatial resolution according to the size of the imaging target site. Moreover, making the pixel values (signal values) of the invalid blocks positioned in what is known as the directly irradiated region, where the radiation detector 10 is directly irradiated by irradiation that has not passed through the imaging subject, invalid enables appropriate Automatic Exposure Control (AEC) to be performed according to the imaging target site. Note that although in the present exemplary embodiment radiation irradiation from the radiation source 211 is stopped when a summation value of the dose data (pixel values) of each of the valid blocks has reached the specific threshold value or above, for example, configuration may be made such that radiation irradiation from the radiation source 211 is stopped when the dose data (pixel values) of one, or of two or more, of the valid blocks has reached the specific threshold value or above.

Defect Map Generation Processing

As described above, in the electronic cassette 1 according to the present exemplary embodiment, the blocks 62 are formed of plural of the radiation dose detection pixels 60B, and the radiation dose detection is performed in block units. Moreover, the block size of the blocks 62 made up of plural of the radiation dose detection pixels 60B can be changed in the electronic cassette 1. The electronic cassette 1 according to the present exemplary embodiment also includes a function to determine the presence or absence of defects in block units and generate a defect map, as described below.

Figure 14:
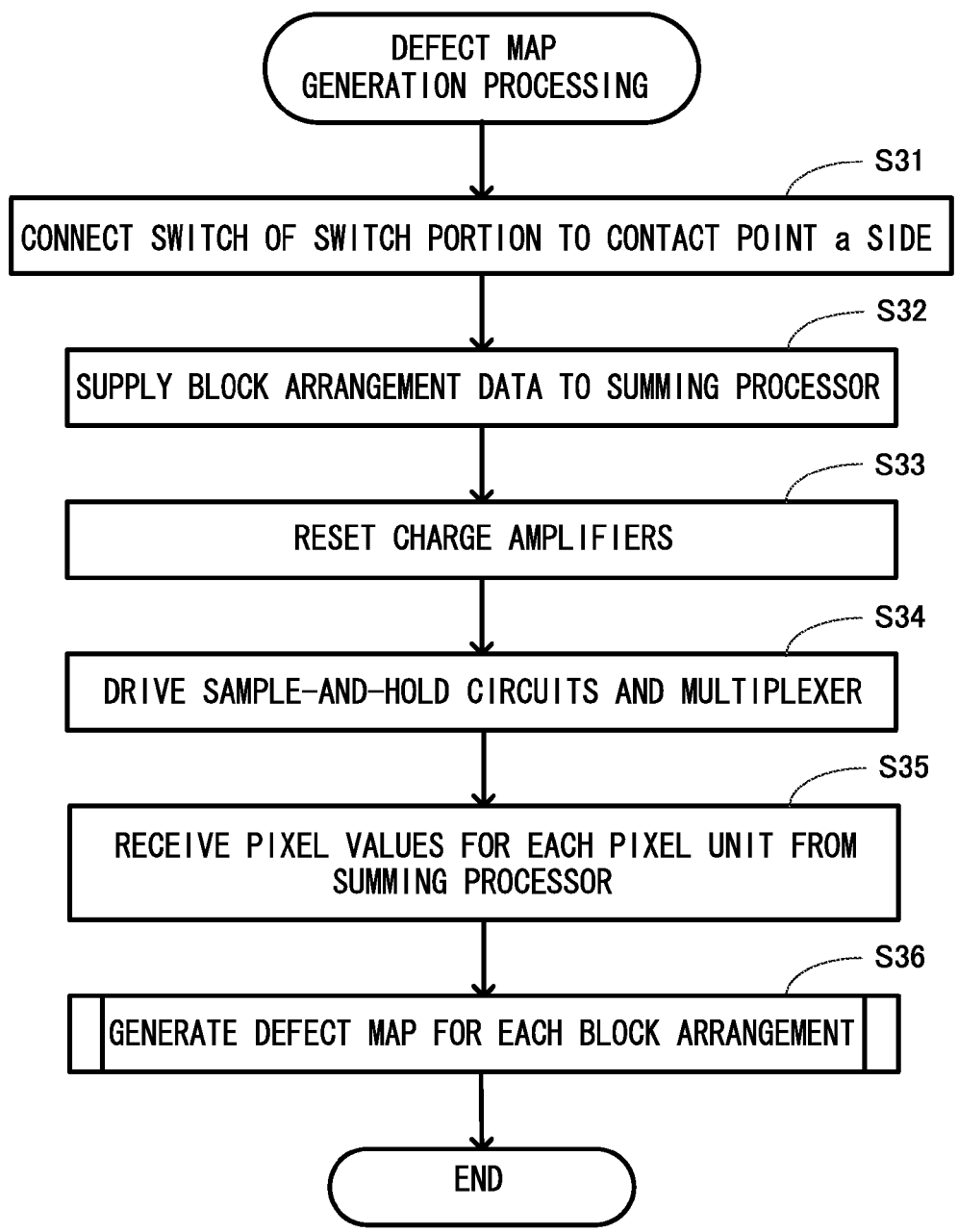
FIG. 14 is a flowchart illustrating a flow of processing in a defect map generation processing program according to an exemplary embodiment of the present invention.

FIG. 14 is a flowchart illustrating a flow of processing in a defect map generation processing program executed by the CPU 26A of the cassette controller 26 of the electronic cassette 1. The program is stored in advance in a specific region of the storage section 26C of the cassette controller 26. The program is, for example, executed based on an input operation to an operation input section such as a switch button, not illustrated in the drawings, provided to the electronic cassette 1, or based on an instruction from the console 230.

At step S31, the CPU 26A of the cassette controller 26 supplies a control signal to the switch portion 245 of the signal processor 24. On receipt of this control signal, the switch portion 245 connects the switch to the contact point a side.

At step S32, the CPU 26A supplies the summing processor 246 of the signal processor 24 with block arrangement data indicating contents of a block arrangement for defect map generation. Note that the block arrangement for defect map generation refers to the block arrangement with the minimum block size. Namely, the summing processor 246 is supplied with block arrangement data indicating the block arrangement in which each of the blocks 62 includes a single pixel unit 61.

At step S33, the CPU 26A supplies a control signal to the charge amplifiers 241 of the signal processor 24. On receipt of this control signal, the charge amplifiers 241 place each of the reset switches 241C in an ON state, thereby resetting the charge amplifiers 241. On completion of charge amplifier 241 reset, the reset switches 241C are driven to an OFF state.

At step S34, the CPU 26A supplies control signals to the sample-and-hold circuits 242 and the multiplexer 243, driving the sample-and-hold circuits 242 and the multiplexer 243 in synchronization with each other. Each of the imaging pixels 60A and each of the radiation dose detection pixels 60B then generate charges on irradiation of the electronic cassette 1 with radiation. All of the TFTs 40 are in the OFF state over the duration in which the electronic cassette 1 is irradiated with radiation, and the charges generated in the imaging pixels 60A accumulate in the capacitors 50. However, the charges generated in the radiation dose detection pixels 60B are input into the charge amplifiers 241 connected to the respective signal lines 22 through the respective signal lines 22. Note that in the electronic cassette 1 of the present exemplary embodiment, charges are read in units of the pixel units 61 configured from plural of the radiation dose detection pixels 60B connected to the same single signal line 22.

Each of the charge amplifiers 241 outputs an output signal according to the amount of charge supplied through the signal line 22. The sample-and-hold circuits 242 sample the output signals of the charge amplifiers 241 at a timing according to a control signal supplied from the CPU 26A of the cassette controller 26. The multiplexer 243 supplies the outputs of the respective sample-and-hold circuits 242 to the A/D converter 244 in sequence. The A/D converter 244 converts the analogue signals sequentially supplied from the multiplexer 243 into digital signals. Namely, the A/D converter 244 sequentially outputs sampled values of the outputs of the respective charge amplifiers 241 as digital values. The output values of the A/D converter 244 are sequentially supplied to the summing processor 246 through the switch portion 245.

The summing processor 246 ascertains the block arrangement based on the block arrangement data supplied from the CPU 26A at step S32, and, for each block, performs processing to sum together the output values from the A/D converter 244 belonging to the same block. The block arrangement data supplied at step S32 indicates the block arrangement in which only a single pixel unit 61 is included in each block, and so at the present step, the summing processor 246 supplies the output value of the A/D converter 244 to the CPU 26A as it is, without performing summing. Namely, the summing processor 246 supplies the pixel value (signal value) of each pixel unit 61 to the CPU 26A.

At step S35, the CPU 26A receives the pixel value (signal value) of each pixel unit 61 from the summing processor 246, and retains the pixel values (signal values) in the memory 26B.

At step S36, for each block arrangement such as those illustrated in FIG. 9A to FIG. 9D, the CPU 26A generates a defect map indicating the presence or absence of defects in each block based on the pixel value (signal value) of each pixel unit 61 stored in the memory 26B.

Figure 15:
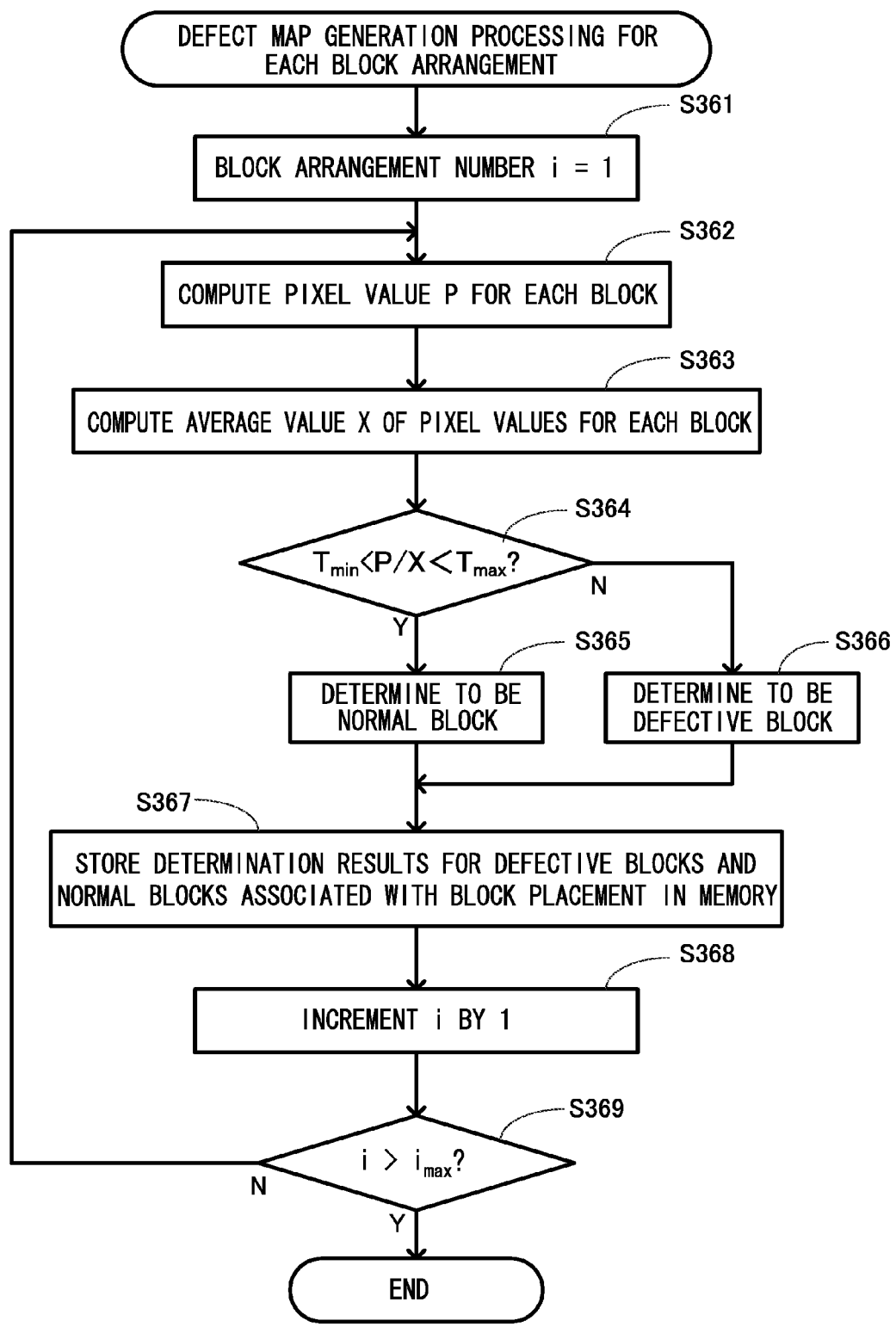
FIG. 15 is a flowchart illustrating a flow of processing in a defect map generation processing program according to an exemplary embodiment of the present invention.

FIG. 15 is a flowchart illustrating details of the processing at step S36. At step S361, the CPU 26A sets a block arrangement number i to 1. The block arrangement numbers are numbers applied for convenience, in order to distinguish between respective block arrangement such as those illustrated in FIG. 9A to FIG. 9D.

At step S362, the CPU 26A computes a pixel value (signal value) P for each block 62 for the block arrangement corresponding to the block arrangement number 1. Namely, from the pixel values for each pixel unit 61 stored in the memory 26B, the CPU 26A computes a value obtained by summing together pixel units 61 belonging to the same block as the pixel value P for that block 62. For example, in a case in which the block arrangement corresponding to the block arrangement number 1 includes a single pixel unit 61 in each block, as illustrated in FIG. 9A, then the pixel values of each of the pixel units 61 stored in the memory 26B are computed as the pixel values P of the respective blocks without any modification. However, in a case in which the block arrangement corresponding to the block arrangement number 1 includes two of the pixel units 61 in each block, as illustrated in FIG. 9B, then, from the pixel values of each of the pixel units 61 stored in the memory 26B, a value obtained by summing together the two pixel values belonging to the same block is computed as the pixel value P for that block 62. In this manner, the CPU 26A computes the pixel values P for each block 62 in the block arrangement corresponding to the block arrangement number 1, based on the pixel values of each of the pixel units 61 stored in the memory 26B.

At step S363, the CPU 26A computes an average value X of the pixel values P computed for each block 62 at step S362.

At step S363, the CPU 26A computes a ratio P/X between the pixel value P computed for each block 62 at step S362, and the average value X computed at step S363, for each block. Then, determination is made as to whether or not the P/X computed for each block satisfies $T_{min} \leq P D/X \leq T_{max}$. $T_{min}$ is, for example, 0.8, and $T_{max}$ is, for example, 1.2. In this case, determination is made as to whether or not the pixel value P falls within a range of from 80% to 120% of the average value X. Note that the values of $T_{min}$ and $T_{max}$ may be varied as appropriate. If determination by the CPU 26A is affirmative at step S363, the block pixels are determined to be a normal block (step S365), and if determination by the CPU 26A is negative, the block is determined to be a defective block (step S366). Namely, blocks that output a pixel value P far exceeding the average value X are determined to be defective blocks. The CPU 26A performs this defect determination for every block.

At step S367, the CPU 26A stores a determination result of "defective block" or "normal block" in the memory 26B associated with the placement of the corresponding block. Defect map generation is thus completed for the block arrangement corresponding to the block arrangement number 1.

At step S368, the CPU 26A increments the value of the block arrangement number i by 1, and at step S369, the CPU 26A determines whether or not the value of i is greater than a number $i_{max}$ of the anticipated block arrangements. If determination is negative at step S369, processing returns to step S362 on the assumption that defect map generation has not yet been completed for all anticipated block arrangements. Next, a defect map is generated for another block arrangement by following the steps described above. When defect map generation has been completed for all other anticipated block arrangements, determination is affirmative at step S369 and the present routine is ended.

The electronic cassette 1 of the present exemplary embodiment accordingly generates respective defect maps indicating the presence or absence of defects in each block for plural anticipated block arrangements. Note that in the present exemplary embodiment, the block defect determination is performed by comparing the pixel value P of each block against the average value X of the pixel values of all of the blocks, however there is no limitation thereto. For example, configuration may be made such that defect determination is performed based on a difference with adjacent peripheral blocks, or defect determination may be performed employing predetermined threshold values for each block arrangement (each block size). Moreover, in the present exemplary embodiment, an example is illustrated in which defect determination is performed based on pixel values when radiation is irradiated, however defect determination may be performed based on pixel values when radiation is not irradiated. Appropriate detection of leaks and defects is possible since dark charge is generated by the radiation dose detection pixels 60B even when radiation is not being irradiated.

Placement Data Notification Processing

The electronic cassette 1 of the present exemplary embodiment includes a function to notify a user of the placement of defective blocks, based on the defect maps generated in the defect map generation processing described above (see FIG. 14, FIG. 15).

Figure 16:
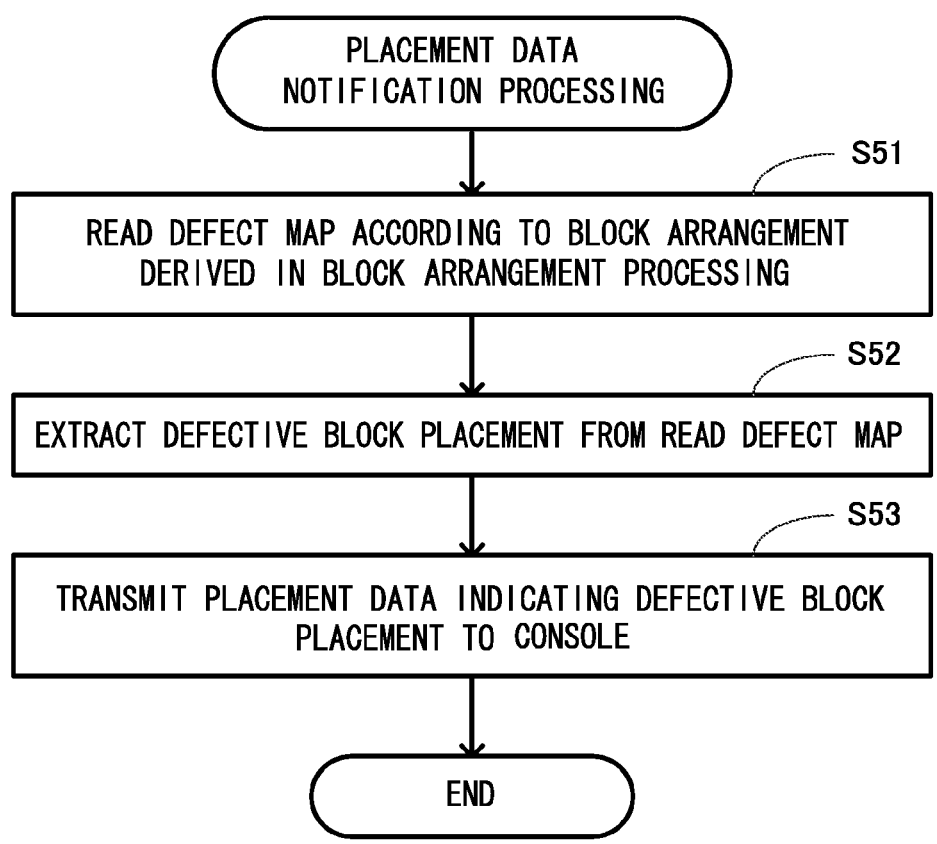
FIG. 16 is a flowchart illustrating a flow of processing in a placement data notification processing program according to an exemplary embodiment of the present invention.

At a timing of completion of the block arrangement processing described above, for example, the electronic cassette 1 executes placement data notification processing, in which placement data indicating the placement of blocks determined to be defective in the defect map generation processing described above is transmitted to the console 230. FIG. 16 is a flowchart illustrating a flow of processing in a placement data notification processing program executed by the CPU 26A of the cassette controller 26 of the electronic cassette 1. The program is stored in advance in a specific region of the storage section 26C of the cassette controller 26. Note that the block arrangement according to the imaging target site is derived in the block arrangement processing described above (see FIG. 10) prior to executing the program.

At step S51, the CPU 26A of the cassette controller 26 reads the defect map corresponding to the block arrangement derived in the block arrangement processing (see FIG. 10) from the memory 26B.

At step S52, the CPU 26A extracts the placement of defective blocks from the defect map read from the memory 26B at step S51.

At step S53, the CPU 26A generates placement data indicating the placement of the extracted defective blocks, and transmits the placement data to the console 230 through the wireless communication section 27. The present routine is then ended.

Figure 17A:
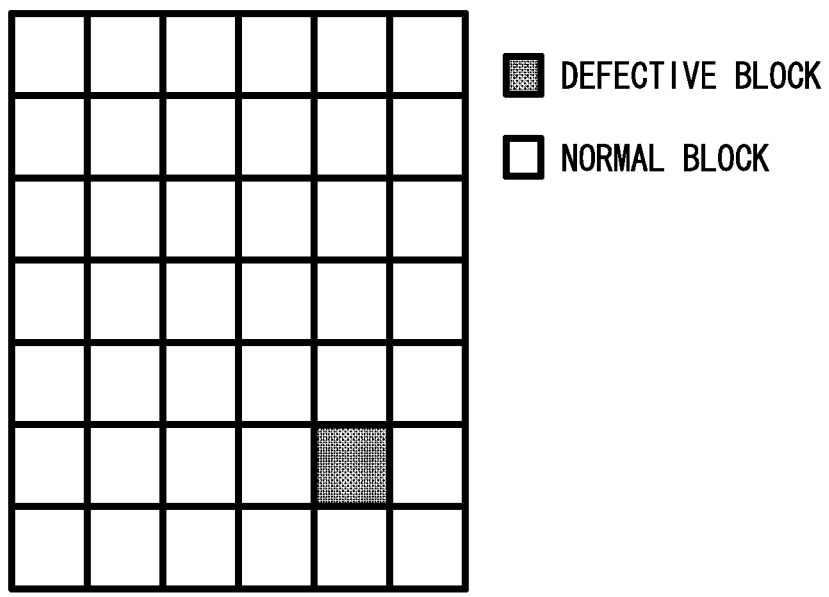
FIG. 17A is a drawing illustrating an example of display of a placement of a defective block according to an exemplary embodiment of the present invention.

The placement data transmitted from the electronic cassette 1 is received by the wireless communication section 239 of the console 230. The CPU 233 of the console 230 drives the display driver 237 to display the placement of defective blocks indicated by the received placement data on the display 231, for example in a configuration such as that illustrated in FIG. 17A. The imaging technician is able to view the placement of defective blocks in the electronic cassette 1 on the display 231. This accordingly enables the imaging technician to take action to position the patient, this being the imaging subject, so as to avoid the defective blocks.

Figure 17B:
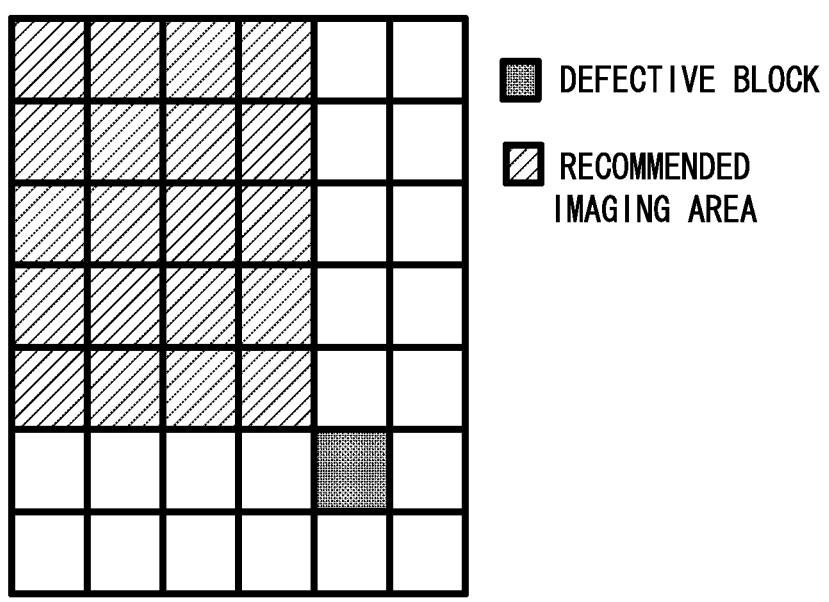
FIG. 17B is a drawing illustrating an example of display of a placement of a defective block and a recommended imaging area according to an exemplary embodiment of the present invention.

Note that in the above exemplary embodiment, the CPU 26A of the cassette controller 26 transmits placement data indicating the placement of defective blocks to the console 230, however configuration may be made such that placement data indicating the placement of normal blocks other than defective blocks, or placement data indicating a recommended imaging area avoiding defective blocks, is transmitted to the console 230. As illustrated in FIG. 17B, the display 231 of the console 230 may display a recommended imaging area avoiding defective blocks instead of displaying the placement of defective blocks, or as well as displaying the placement of defective blocks. Moreover, in the exemplary embodiment described above, the display 231 of the console 230 displays the placement of defective blocks, however a display section may be provided to the electronic cassette 1, with the placement of defective blocks and the like displayed on this display section. Moreover, the number of defective blocks may be totaled for each divided area obtained by dividing a detection face of the radiation detector into plural regions, and setting one, or two or more, of the divided areas that contain comparatively few defective blocks as a recommended imaging area, and then transmitting placement data indicating the recommended imaging area to the console 230. Moreover, one, or two or more, divided areas in which the number of defective blocks exceed a specific value may be set as an imaging prohibited area, and placement data indicating the imaging prohibited area transmitted to the console 230.

Block Rearrangement Processing

The electronic cassette 1 according to the present exemplary embodiment includes a block rearrangement function to modify the arrangement of the blocks in response to an instruction or the like from the imaging technician in a case in which defective blocks are present in any of the blocks 62 arranged in the block arrangement processing described above (see FIG. 10).

Figure 18A:
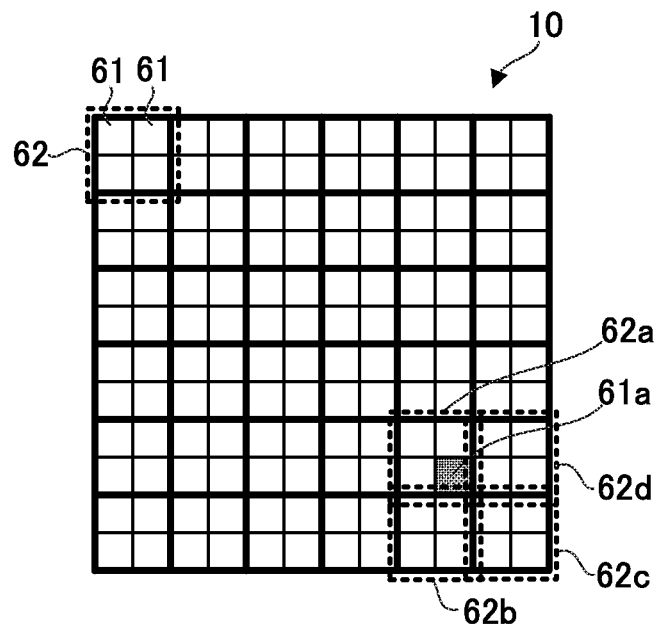
FIG. 18A is a drawing illustrating contents of the first block rearrangement processing according to an exemplary embodiment of the present invention.
Figure 18B:
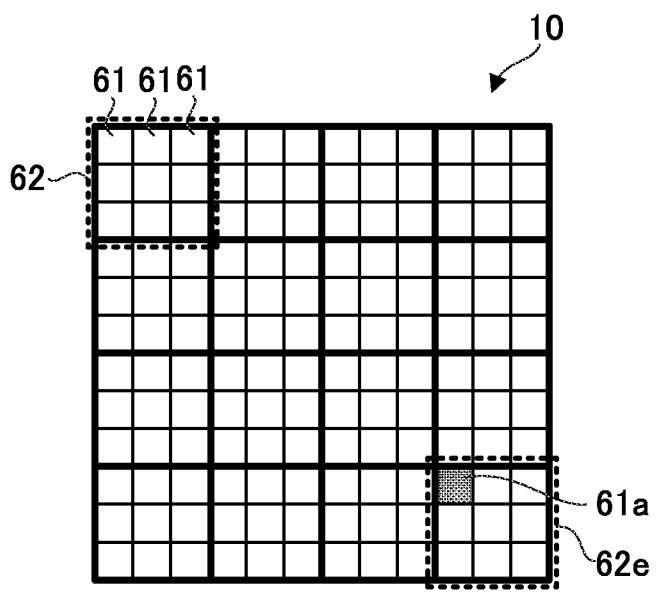
FIG. 18B is a drawing illustrating contents of the first block rearrangement processing according to an exemplary embodiment of the present invention.

FIG. 18A and FIG. 18B illustrate contents of first block rearrangement processing executed by the CPU 26A of the cassette controller 26 of the electronic cassette 1. FIG. 18A illustrates an example of a block arrangement of the radiation dose detection pixels 60B prior to rearrangement processing. Namely, in the block arrangement illustrated in FIG. 18A, the arrangement is configured based on the imaging target site in block arrangement processing (see FIG. 10) by the electronic cassette 1. FIG. 18B illustrates an example of a block arrangement in which the block arrangement illustrated in FIG. 18A has been rearranged.

The example illustrated in FIG. 18A illustrates a block arrangement including 4 of the pixel units 61 in each block 62. Moreover, in this example, the pixel unit 61a in the block 62a contains a defective pixel, while the other three pixel units in the block 62a are normal. The block 62a has been determined to be a defective block in the defect map generation processing described above. In the electronic cassette 1 according to the present exemplary embodiment, the pixel values (signal values) obtained from defective blocks are treated as invalid in a case in which radiation dose detection is performed in block units, and so from the perspective of performing appropriate automatic exposure control (AEC) it is not desirable to place the imaging subject over defective blocks. Accordingly, if defective blocks are present in the radiation detector 10, there is a need to take action to position the imaging subject avoiding the defective blocks. However, depending on the placement of defective blocks, sometimes defective blocks fall in-between normal blocks, such that positioning that avoids the defective blocks becomes difficult. For example, in the example illustrated in FIG. 18A, it is difficult to employ the blocks 62b, 63c, and 62d that are adjacent to the block 62a as normal blocks.

The block rearrangement processing illustrated in FIG. 18B is accordingly executed in a case in which the CPU 26A of the cassette controller has, for example, been notified from the console 230 of an instruction to rearrange the block 62. In FIG. 18B, the original block arrangement illustrated in FIG. 18A has been modified to enlarge the block size of each of the blocks 62 with respect to the original block arrangement illustrated in FIG. 18A. Namely, the block arrangement in which four of the pixel units 61 are included in a single block 62 (FIG. 18A) has been modified to a block arrangement in which nine of the pixel units 61 are included in a single block 62 (FIG. 18B). Performing block rearrangement while changing the block size moves the placement of the defective block in the radiation detector 10, with the possibility of securing contiguous normal block areas of comparatively large surface area. Positioning of the imaging subject may sometimes be made easier as a result. In the examples illustrated in FIG. 18A and FIG. 18B, the pixel unit 61a containing the defective pixel that belonged to the block 62a in the original block arrangement now belongs to the newly arranged block 62e. In this case, although it is possible that the block 62e may be determined to be a defective block, since the position of the defective block has moved to a corner portion of the radiation detector 10, a contiguous normal block area of comparatively large surface area can be secured. It is accordingly easier to perform radiation dose detection employing only normal blocks, and avoiding the defective block.

In the electronic cassette 1 according to the present exemplary embodiment, a value obtained by summing the pixel values (signal values) from all of the pixel units 61 in a block is computed as the pixel value (signal value) P of that block, and defect determination for the block is performed based on the pixel value P. Accordingly, by performing block rearrangement to enlarge the block size, the effect on the block of the pixel unit 61 containing the defective pixel becomes relatively small. The likelihood of the block being determined to be a defective block accordingly decreases following block rearrangement. Namely, in a case in which blocks determined to be defective blocks are present prior to block rearrangement, there is a possibility that blocks determined to be defective blocks no longer appear or decrease in number due to performing block rearrangement to enlarge the block size. Reducing the number of blocks determined to be defective blocks enables radiation dose detection employing only normal blocks, avoiding defective blocks, to be performed more easily. Note that the examples illustrated in FIG. 18A and FIG. 18B illustrate a case in which the block size is enlarged, however the blocks 62 may be rearranged such that the block size is reduced. In a case in which the block size is reduced, there is a possibility that the placement of defective blocks may move, thereby facilitating radiation dose detection employing only normal blocks, avoiding defective blocks.

Figure 19A:
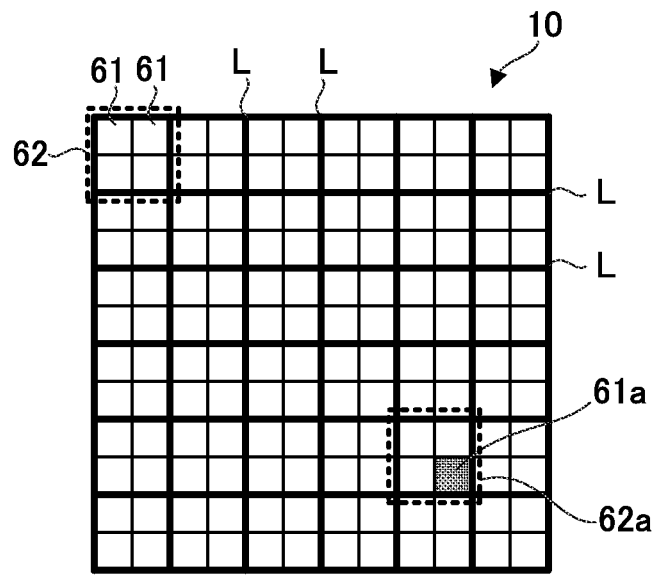
FIG. 19A is a drawing illustrating contents of the second block rearrangement processing according to an exemplary embodiment of the present invention.
Figure 19B:
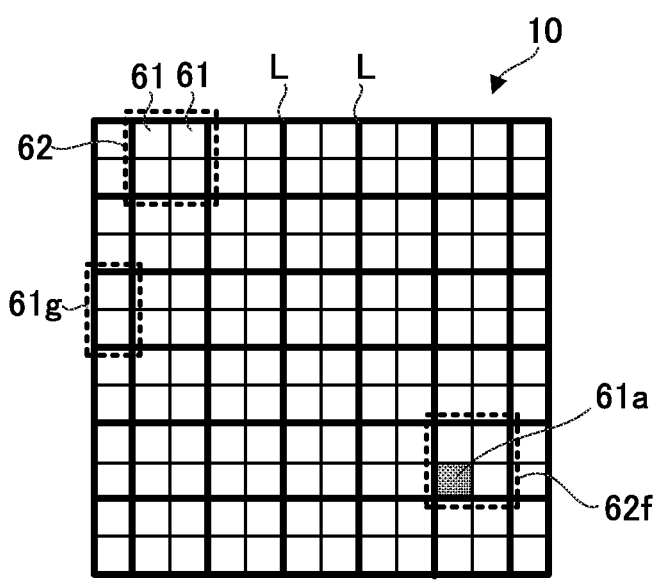
FIG. 19B is a drawing illustrating contents of the second block rearrangement processing according to an exemplary embodiment of the present invention.

FIG. 19A and FIG. 19B illustrate contents of second block rearrangement processing executed by the CPU 26A of the cassette controller 26 of the electronic cassette 1. FIG. 19A illustrates an example of a block arrangement of the radiation dose detection pixels 60B prior to rearrangement processing. Namely, in the block arrangement illustrated in FIG. 19A, the arrangement is configured based on the imaging target site in block arrangement processing (see FIG. 10) by the electronic cassette 1. FIG. 19B illustrates an example of a block arrangement in which the block arrangement illustrated in FIG. 19A has been rearranged.

The block arrangement illustrated in FIG. 19A is similar to the block arrangement illustrated in FIG. 18A, described above. In this example, once again the pixel unit 61a in the block 62a contains a defective pixel, and the other three pixel units in the block 62a are normal. The block 62a has been determined to be a defective block in the defect map generation processing described above.

The block rearrangement processing illustrated in FIG. 19B is executed in a case in which the CPU 26A of the cassette controller 26 has, for example, been notified from the console 230 of an instruction to perform block rearrangement. Namely, the CPU 26A of the cassette controller 26 moves inter-block boundaries defining the respective blocks 62, without changing the block size from the block arrangement illustrated in FIG. 19A. Namely, the CPU 26A performs block rearrangement by shifting boundary lines L separating mutually adjacent blocks. FIG. 19B illustrates an example in which the boundary lines L of the blocks 62 are shifted in a sideways direction by one pixel unit, however the shift amount and shift direction of the boundary lines L may be varied as appropriate. Such block rearrangement processing enables the placement of defective blocks to be moved while maintaining the block size. In the example illustrated in FIG. 19A and FIG. 19B, the pixel unit 61a containing a defective pixel, that belonged to the block 62a in the original block arrangement now belongs to the newly arranged block 62f. Moving the placement of the defective blocks in this manner gives the possibility of securing contiguous normal block areas of comparatively large surface area, with the possibility of facilitating positioning as a result. Note that the above explanation illustrates the block boundary lines L to aid understanding, however in reality, the CPU 26A performs processing to modify the combinations of the pixel units 61 included in the same block.

Figure 20A:
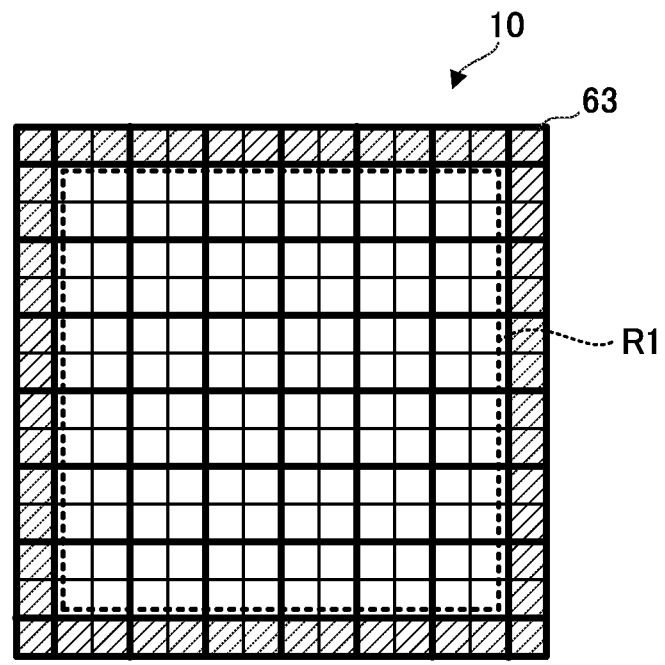
FIG. 20A is a drawing illustrating a configuration of a radiation detector according to an exemplary embodiment of the present invention.
Figure 20B:
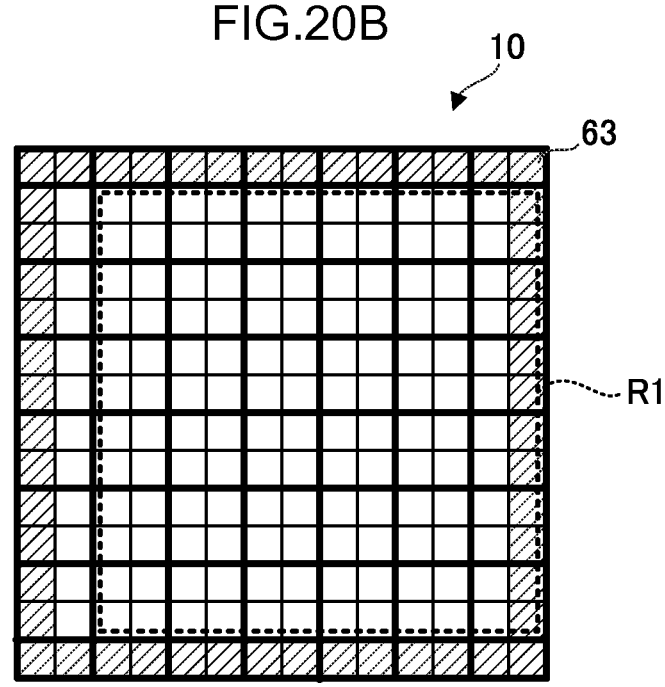
FIG. 20B is a drawing illustrating a configuration of a radiation detector according to an exemplary embodiment of the present invention.

Note that in a case in which the block boundary lines L are shifted as illustrated in FIG. 19B, sometimes the total number of blocks in the radiation detector 10 changes, accompanied by a change in the block size of blocks positioned at outer peripheral portions of the radiation detector 10, such as the block 61g. Such changes in the total number of blocks in the radiation detector 10, and the presence of blocks of different sizes, complicates processing during radiation dose detection performed in block units, defect determination, image generation, described later, and the like. Therefore, as illustrated in FIG. 20A, a buffer region 63 (illustrated by hatching) with a width of one, or two or more, pixel units is preferably provided at outer peripheral portions of a block group in the radiation detector 10. Plural of the radiation dose detection pixels 60B formed in the buffer region 63 are set as a invalid region not employed in radiation dose detection and the like in the block arrangement prior to performing rearrangement. A valid region R1 employed in radiation dose detection and the like is configured inside the buffer region 63. In a case in which the position of the boundary lines L of the blocks 62 are shifted in block rearrangement processing, a portion of the buffer region 63 is incorporated into the valid region R1, as illustrated in FIG. 20B. Providing such a buffer region 63, that is not normally employed, at the outer peripheral portions of the radiation detector 10 enables changes in the total number of the blocks 62, and the presence of blocks of different sizes, in the radiation detector 10 to be prevented by appropriately employing the buffer region 63 in a case in which the boundary lines L of the blocks 62 have been shifted in block rearrangement processing. Note that in the present exemplary embodiment, explanation has been given regarding a case in which the block rearrangement processing is performed if there is notification from the console 230 of an instruction to perform rearrangement of the blocks 62, however block rearrangement may also be performed in a case in which defective blocks are detected in the defect map generation processing described above (see FIG. 14).

Radiographic Image Capture Processing

Figure 21:
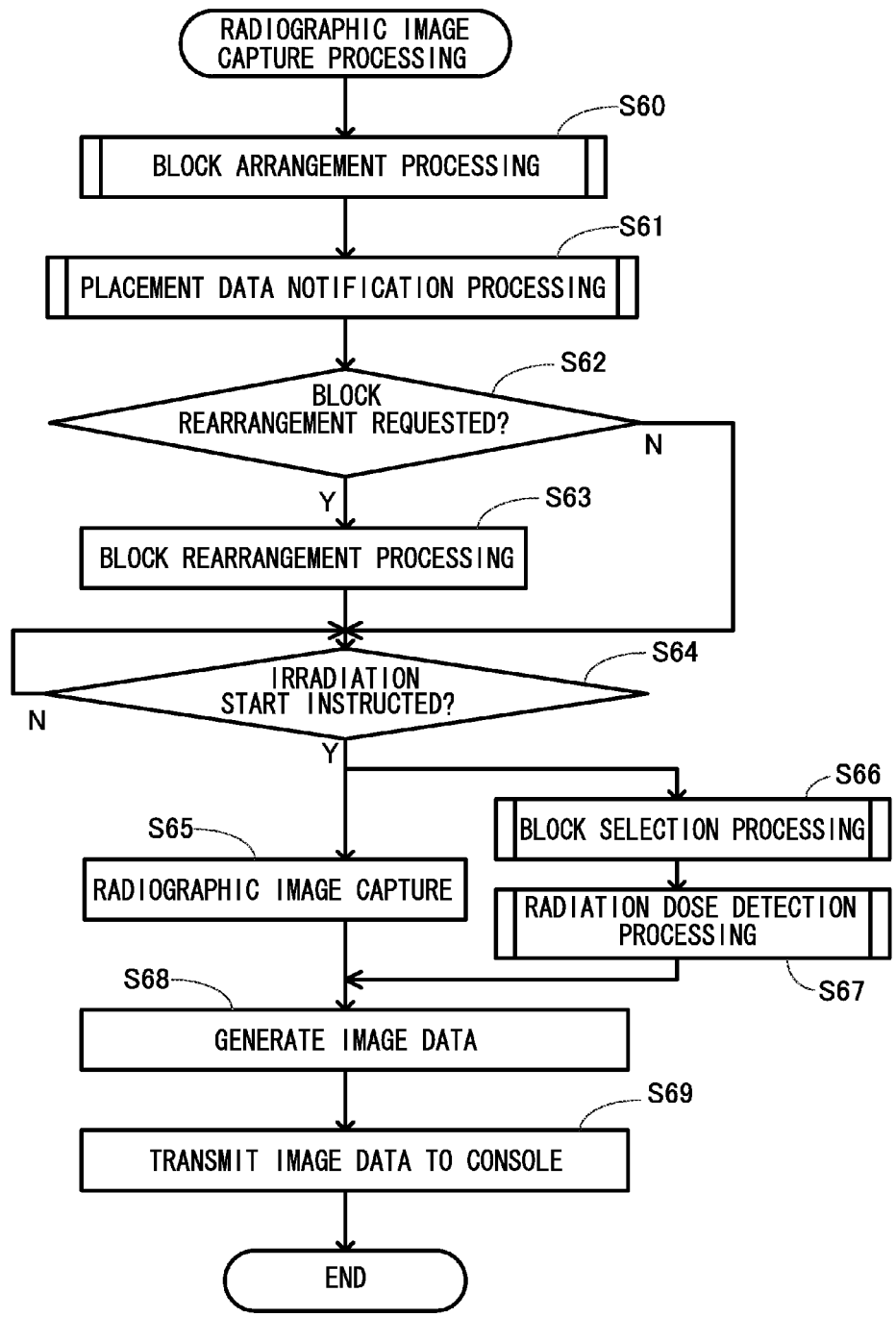
FIG. 21 is a flowchart illustrating a flow of processing in a radiographic image capture processing program according to an exemplary embodiment of the present invention.

Explanation follows regarding radiographic image capture processing to capture diagnostic radiographic images using the imaging pixels 60A in the electronic cassette 1. FIG. 21 is a flowchart illustrating a flow of processing in a radiographic image capture processing program executed by the CPU 26A of the cassette controller 26 of the electronic cassette 1. Note that the defect map generation processing program (see FIG. 14, FIG. 15) described above is executed, and defect maps for each anticipated block arrangement are stored in the memory 26B of the cassette controller 26, prior to execution of the radiographic image capture processing program.

During diagnostic radiographic image capture employing the electronic cassette 1, the display 231 of the console 230 displays the initial data input screen for input of the specific initial data. The initial data input screen displays messages prompting input of the name of the patient (imaging subject) for radiographic image capture, imaging target site, posture during imaging, and exposure conditions such as tube voltage and tube current during radiation exposure, and displays input regions for the initial data. The imaging technician inputs the specific initial data of the initial data input screen using the operation panel 232.

The initial data described above is transmitted from the console 230 to the electronic cassette 1 using the wireless communication section 239. The exposure conditions included in the initial data are transmitted to the radiation generator 210 using the wireless communication section 239. In response, the controller 212 of the radiation generator 210 performs preparation for exposure at the received exposure conditions.

On receipt of the above initial data from the console 230, the electronic cassette 1 executes the radiographic image capture processing program.

At step S60, the CPU 26A of the cassette controller 26 executes the block arrangement processing described above (see FIG. 10). In the block arrangement processing, the block arrangement is derived according to the imaging target site indicated by the initial data supplied from the console 230.

At step S61, the CPU 26A executes the placement data notification processing described above (see FIG. 16). The placement of defective blocks in the block arrangement is accordingly displayed on the display 231 of the console 230. The imaging technician can accordingly confirm the placement of defective blocks displayed on the display 231 of the console 230, and then use the operation panel 232 to instruct whether or not to perform block rearrangement of the blocks 62.

Then at step S62, the CPU 26A of the cassette controller 26 determines whether or not block rearrangement has been requested from the console 230. If block rearrangement processing has been requested from the console 230, then at step S63, the CPU 26A performs block rearrangement processing such as that illustrated in FIG. 18A and FIG. 18B, or in FIG. 19A and FIG. 19B. However, processing transitions to step S64 without the CPU 26A rearranging the blocks 62 if block rearrangement has not been requested from the console 230.

At step S64, the CPU 26A performs standby for a radiation irradiation start instruction from the console 230. Processing transitions to step S65 on receipt of the radiation irradiation start instruction by the CPU 26A.

At step S65, the CPU 26A starts diagnostic radiographic image capture using the imaging pixels 60A. Specifically, the CPU 26A supplies a control signal to the gate line driver 23 to place all of the TFTs 40 in the OFF state. The imaging pixels 60A accordingly start to accumulate charges generated in response to irradiated radiation, and transition is made to radiographic image capture operation.

At step S66, performed in parallel to the diagnostic radiographic image capture using the imaging pixels 60A, the CPU 26A executes the block selection processing described above (see FIG. 12). A simple radiographic image is captured using the radiation dose detection pixels 60B, and the imaging subject region is identified based on the obtained radiographic image. The valid blocks and invalid blocks are then set such that the identified imaging subject region and the range of the valid blocks overlap with each other.

On completion of block selection processing at step S66, at step S67 the CPU 26A executes the radiation dose detection processing described above (see FIG. 13). Namely, the cumulative radiation dose is detected by the radiation dose detection pixels 60B, in parallel to charge accumulation in the imaging pixels 60A. The cumulative radiation dose detection is performed in block units for the blocks arranged at step S60 or the blocks rearranged at step S63. At step S67, the CPU 26A transmits a radiation dose detection signal to the console 230 in a case in which the CPU 26A has determined that the summation value of the dose data (pixel values) of each of the valid blocks of the radiation dose detection pixels 60B exceeds the specific threshold value. On receipt of the radiation dose detection signal, the CPU 233 of the console 230 supplies the radiation generator 210 with instruction data instructing radiation irradiation stop. On receipt of this control signal, the radiation generator 210 stops radiation irradiation. Note that charge accumulation in the imaging pixels 60A continues until completion of the present step.

At step S68, the CPU 26A reads the accumulated charges in the imaging pixels 60A to generate a diagnostic radiographic image. Specifically, the CPU 26A supplies a control signal to the switch portion 245 of the signal processor 24 such that the switch of the switch portion 245 connects on the contact point b side, and the CPU 26A also supplies a control signal to the gate line driver 23 so as to output ON signals from the gate line driver 23 to each of the gate lines 21 in sequence one line at a time, and the respective TFTs 40 connected to each of the gate lines 21 are placed in the ON state in sequence one line at a time. The accumulated charges in the capacitors 50 of the imaging pixels 60A are accordingly read into the respective signal lines 22, converted into digital signals in the signal processor 24, and supplied to the CPU 26A. The CPU 26A generates diagnostic image data based on the digitalized pixel values (signal values) of the imaging pixels 60A, which is then stored in the image memory 25.

At step S69, the CPU 26A reads the image data stored in the image memory 25, and transmits the read image data to the console 230 using the wireless communication section 27. The present routine is then ended.

In the console 230, the image data supplied from the electronic cassette 1 is stored in the HDD 236, and a radiographic image expressed by this image data is displayed on the display 231. The console 230 moreover transmits the image data to the RIS server 104 through the in-hospital network 110. The image data transmitted to the RIS server 104 is stored in the database 104A.

The electronic cassette 1 according to the present exemplary embodiment enables capture of a simple radiographic image to identify the imaging subject region using the radiation dose detection pixels 60B within the duration of diagnostic radiographic image capture using the imaging pixels 60A. This accordingly enables both setting of the range of the valid blocks, and generation of a diagnostic radiographic image to be performed at a single time of radiation irradiation.

Treatment of Defective Blocks

In the electronic cassette 1 according to the present exemplary embodiment, in a case in which the arranged blocks 62 of the radiation dose detection pixels 60B contain defective blocks, the dose data (pixel values) from the defective blocks may be treated as invalid in the radiation dose detection processing to detect the cumulative radiation dose.

Figure 22:
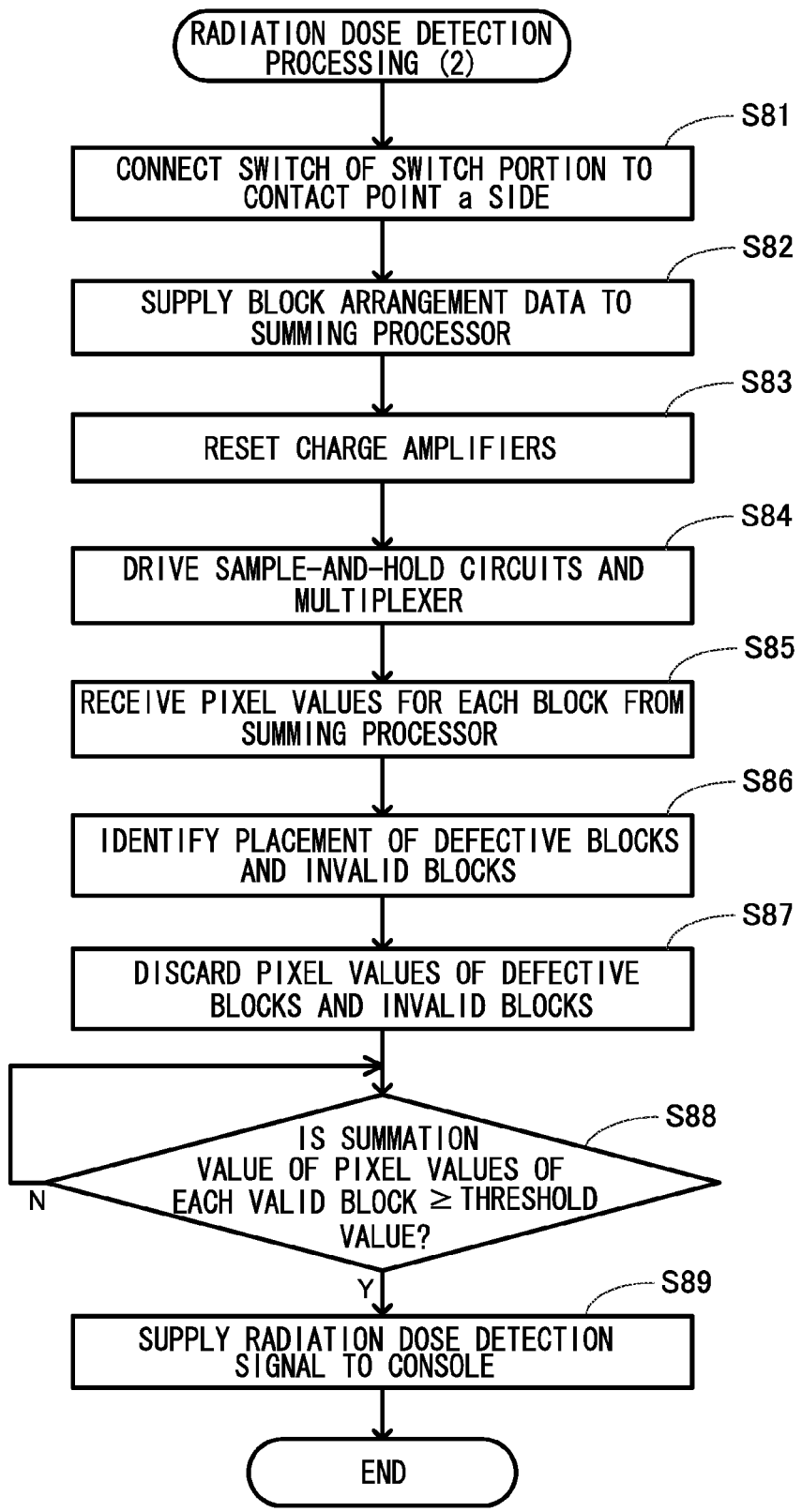
FIG. 22 is a flowchart illustrating a flow of processing in a second radiation dose detection processing program according to an exemplary embodiment of the present invention.

FIG. 22 is a flowchart illustrating a flow of processing in a second radiation dose detection processing program implementing the radiation dose detection processing. Note that the defect map generation processing program (see FIG. 14, FIG. 15) described above is executed, and defect maps for each anticipated block arrangement are stored in the cassette controller 26, prior to execution of the second radiation dose detection processing program.

Note that the processing of step S81 to step S85 is similar to the processing of step S21 to step S25 of the first radiation dose detection processing (see FIG. 13), and so further explanation thereof is omitted.

At step S86, the CPU 26A of the cassette controller 26 reads the placement of the invalid blocks not to be used in radiation dose detection stored in the memory 26B at step S15 of the block arrangement processing described above (see FIG. 10). The CPU 26A also reads from the memory 26B the defect map corresponding to the block arrangement stored in the memory 26B at step S36 of the defect map generation processing described above (see FIG. 14, FIG. 15). The CPU 26A accordingly identifies the placement of the invalid blocks and defective blocks.

At step S87, the CPU 26A excludes or discards dose data (pixel values) corresponding to the invalid blocks and defective blocks identified at step S86 from the dose data (pixel values) of each block supplied from the summing processor 246 at step S85.

At step S88, the CPU 26A determines whether or not a summation value of the dose data (pixel values) of each of the valid blocks that remain is a specific threshold value or above. The electronic cassette 1 uses this determination to detect that the cumulative radiation dose of radiation irradiated onto the imaging face of the radiation detector 10 through the imaging subject has reached the specific value. Processing transitions to step S89 in a case in which the CPU 26A determines that the summation value of the dose data (pixel values) from each of the valid blocks excluding the defective blocks has reached the specific threshold value or above.

At step S89, the CPU 26A generates a radiation dose detection signal indicating that the cumulative radiation dose with which the electronic cassette 1 has been irradiated has reached the specific value or above, and supplies the radiation dose detection signal to the console 230. The present routine is then ended. Note that although in the present exemplary embodiment, radiation irradiation from the radiation source 211 is stopped when the summation value of the dose data (pixel values) from each of the valid blocks, excluding the defective blocks, has reached the specific threshold value or above, configuration may be made, for example, such that radiation irradiation from the radiation source 211 is stopped when the dose data (pixel values) of one, or of two or more, of the valid blocks excluding the defective blocks has reached the specific threshold value or above.

Accordingly, in the second radiation dose detection processing according to the present exemplary embodiment, the pixel values of the invalid blocks positioned in what is known as the directly irradiated region where the radiation detector 10 is directly irradiated by irradiation that has not passed through the imaging subject, and the pixel values of the defective blocks, are excluded from determination in cumulative radiation dose detection. This accordingly enables cumulative radiation dose detection to be performed using only the normal blocks out of the valid blocks. Namely, cumulative radiation dose detection based on abnormal pixel values of the defective blocks is prevented, enabling appropriate automatic exposure control (AEC) to be performed.

Note that the electronic cassette 1 may be configured such that either the first radiation dose detection processing described above (see FIG. 13), in which pixel values from defective blocks are not made invalid and are included in determination in cumulative radiation dose detection, or the second radiation dose detection processing described above (see FIG. 22) is selectable. Namely, the electronic cassette 1 may be configured so as to enable selection between a first mode, in which defective blocks are also used in cumulative radiation dose detection, and a second mode in which cumulative radiation dose detection is performed using only normal blocks, without using defective blocks. For example, in a case in which defective blocks exhibit minor defects such as leakage or a drop in output, sometimes more accurate radiation dose detection can be performed by performing cumulative radiation dose detection with the defective blocks included. However, more accurate radiation dose detection can be performed by employing only normal blocks without employing the defective blocks in a case in which the defective blocks exhibit serious defects such as shorting or becoming stuck open. Making the two modes described above selectable enables either mode to be selected according to the level of defects, thereby enabling more appropriate cumulative radiation dose detection. Note that selection of the two modes described above may, for example, be performed on receipt of a selection instruction supplied from the console 230 by the wireless communication section 27 of the electronic cassette 1.

Moreover, the pixel values of defective blocks determined to be defective in the defect map generation processing (see FIG. 14) may be corrected using the pixel values of adjacent normal blocks that are peripheral to the defective block. For example, the pixel value of a defective block may be overwritten with the pixel value of a normal block adjacent to the defective block. Alternatively, the pixel value of a defective block may be overwritten with an average value of the pixel values of plural blocks adjacent to the defective block. Such correction processing may also be performed in pixel unit 61 units. Namely, in the defect map generation processing described above (see FIG. 14), the presence or absence of defects may be determined for each pixel unit 61, this being the minimum unit, for the blocks 62 of the radiation dose detection pixels 60B. Accordingly, a pixel unit 61 determined to be defective may be corrected using the pixel value of an adjacent normal pixel unit 61, prior to performing block arrangement.

In the electronic cassette 1 according to the present exemplary embodiment, the pixel values of defective blocks are set as invalid, or are corrected, such that radiation dose detection is not performed employing only the pixel values (signal values) of defective blocks.

As described above, in the electronic cassette 1 according to the present exemplary embodiment, the radiation dose detection pixels 60B are not only employed in cumulative radiation dose detection of irradiated radiation, but are also employed to capture a simple radiographic image to identify the imaging subject region. Note that in a case in which defective blocks are present among the blocks 62 of the radiation dose detection pixels 60B, an appropriate cumulative radiation dose cannot be obtained from the pixel values (signal values) of the defective blocks. Accordingly, the pixel values of defective blocks are preferably treated as invalid as in the second radiation dose detection processing described above (see FIG. 22). Namely, defective blocks are preferably not employed in a case in which the radiation dose detection pixels 60B are used for cumulative radiation dose detection. However, in a case in which the radiation dose detection pixels 60B are used to capture a simple radiographic image in order to identify the imaging subject region, the effect on image quality is limited even if correct pixel values are not obtainable from defective blocks, and so often no issues arise with regards to identifying the imaging subject region.

Accordingly, in the electronic cassette 1 according to the present exemplary embodiment, in a case in which a defect arises in any of the blocks 62 arranged from the radiation dose detection pixels 60B, the pixel values (signal values) of the defective blocks are treated as valid in a case in which the radiation dose detection pixels 60B are being used to capture a simple radiographic image, however the pixel values of the defective blocks are treated as invalid in a case in which the radiation dose detection pixels 60B are being used in cumulative radiation dose detection. Specifically, in the block selection processing at step S66 of the radiographic image capture processing program illustrated in FIG. 21, in a case in which the radiation dose detection pixels 60B are being used to capture a simple radiographic image in order to identify the imaging subject region, the pixel values of defective blocks are treated as valid and processed to generate a radiographic image rather than being discarded. Supposing the pixel values of defective blocks were to be treated as invalid, image portions corresponding to the defective blocks would be missing, lowering the image quality and sometimes making identification of the imaging subject region difficult. Due to treating the pixel values of defective blocks as valid, as in the present exemplary embodiment, although the correct pixel values cannot be obtained, the image portions corresponding to the defective blocks are not completely missing, thereby suppressing the drop in image quality, and facilitating identification of the imaging subject region. However, in a case in which the radiation dose detection pixels 60B are being employed in cumulative radiation dose detection in the radiation dose detection processing at step S67 of the radiographic image capture processing program illustrated in FIG. 21, the dose data (pixel values) from the defective blocks is excluded or discarded, and cumulative radiation dose detection is performed using only dose data (pixel values) from the normal blocks. Treating the dose data (pixel values) from the defective blocks as invalid in this manner enables cumulative radiation dose detection to be performed more accurately.

Note that the electronic cassette 1 may be configured so as to enable selection between either the first mode, in which the pixel values (signal values) from the defective blocks are treated as valid, as described above, or the second mode, in which the pixel values from the defective blocks are treated as invalid, during capture of the simple radiographic image using the radiation dose detection pixels 60B. In a case in which the abnormal pixel values from the defective blocks cause a pronounced drop in image quality, making identification of the imaging subject region difficult, sometimes identification of the imaging subject region may become possible by selecting the second mode to leave out the image portions corresponding to the defective blocks. Note that selection of the two modes described above may, for example, be performed on receipt of a selection instruction supplied from the console 230 by the wireless communication section 27 of the electronic cassette 1.

Threshold Value Adjustment Processing

In a case in which defective blocks are included among the valid blocks, the electronic cassette 1 according to the present exemplary embodiment treats the dose data (pixel values) from the defective blocks as invalid in the second radiation dose detection processing illustrated in FIG. 22. However, when making determination as to whether or not the summation value of the dose data (pixel values) from each of the valid blocks excluding defective blocks is the specific threshold value or above at step S88 of the radiation dose detection processing, if defective blocks are included in the valid blocks, the summation values vary according to the number of defective blocks. Accurate detection that the cumulative radiation dose has reached the specific value can therefore not be made if the threshold value is a fixed value. The electronic cassette 1 according to the present exemplary embodiment accordingly includes a threshold value adjustment function to vary the threshold value according to the occurrence state of defective blocks.

In the electronic cassette 1 according to the present exemplary embodiment, the threshold value for determining whether or not the cumulative radiation dose of radiation irradiated onto the radiation detector 10 through the imaging subject has reached the specific value or above is adjusted in the following manner, according to the occurrence state of defective blocks. Namely, the CPU 26A of the cassette controller 26 sets the threshold value by referring to a reference table 501 such as that illustrated in FIG. 23. Threshold values t for a single pixel unit 61 of the radiation dose detection pixels 60B are defined for each imaging target site in the reference table 501. The reference table 501 is stored in a specific region of the storage section 26C of the cassette controller 26.

The CPU 26A of the cassette controller 26 identifies the imaging target site based on, for example, the initial data supplied from the console 230 or on a radiographic image captured by the radiation dose detection pixels 60B, and searches the reference table 501 using the identified imaging target site as a key to extract the threshold value t per single pixel unit corresponding to the imaging target site. At step S88 of the second radiation dose detection processing (see FIG. 22), the CPU 26A derives a threshold value T by solving the following Equation (1), in which S is the block size (the number of pixel units contained in a single block) for the block arrangement derived in the block arrangement processing (see FIG. 10), Ne is the number of valid blocks, and Nd is the number of defective blocks among the valid blocks determined to be defective in the defect map generation processing (see FIG. 14).

$$T = t \times S \times (Ne - Nd) \quad \text{Equation (1)}$$

Accordingly, the threshold value setting processing according to the present exemplary embodiment enables cumulative radiation dose detection to be performed using an appropriate threshold value according to the occurrence state of defective blocks. Appropriate automatic exposure control (AEC) can accordingly be performed as a result.

Valid Block Reset Processing

In a case in which defective blocks are included among the valid blocks in the electronic cassette 1 according to the present exemplary embodiment, the dose data (pixel values) from the defective blocks is treated as invalid in radiation dose detection processing, as illustrated in FIG. 22. Accordingly, in a case in which most of the valid blocks are defective blocks, there is a concern of not being able to perform appropriate cumulative radiation dose detection. Accordingly, the electronic cassette 1 according to the present exemplary embodiment includes a valid block reset function to reset the valid blocks in a case in which the proportion of valid blocks that are defective blocks has reached a specific value or above.

Figure 24:
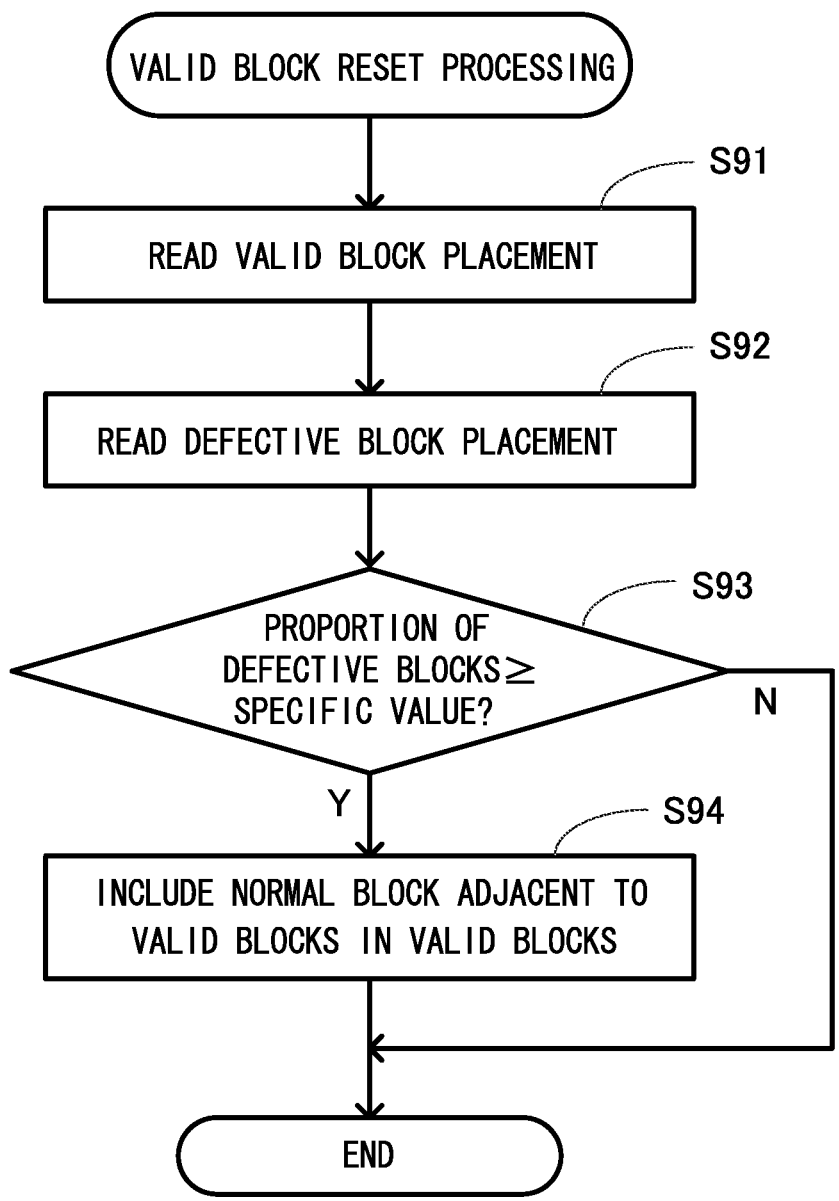
FIG. 24 is a flowchart illustrating a flow of processing in a valid block reset processing program according to an exemplary embodiment of the present invention.

FIG. 24 is a flowchart illustrating a flow of processing in a valid block reset processing program executed by the CPU 26A of the cassette controller 26. The program is stored in advance in a specific region of the storage section 26C of the cassette controller 26. The program is, for example, executed following on from the block arrangement processing program (see FIG. 10).

At step S91, the CPU 26A of the cassette controller 26 reads data indicating the placement of valid blocks set in the block selection processing described above (see FIG. 12) from the memory 26B.

At step S92, the CPU 26A reads data indicating the placement of defective blocks determined to be defective in the defect map generation processing described above (see FIG. 14, FIG. 15) from the memory 26B.

At step S93, the CPU 26A determines whether or not the proportion of defective blocks among the valid blocks is higher than a specific value (for example, 50%) based on the respective data indicating the placement of the valid blocks and the placement of the defective blocks read from the memory 26B. In a case in which the CPU 26A determines that the proportion of defective blocks among the valid blocks is higher than the specific value at the present step, processing transitions to step S94, and in a case in which the CPU 26A determines that the proportion of defective blocks among the valid blocks is lower than the specific value, the present routine is ended.

At step S94, the CPU 26A sets normal blocks adjacent to the valid blocks as new valid blocks, and stores the placement of the new valid blocks in the memory 26B. The present routine is then ended.

Resetting the valid blocks in this manner enables appropriate cumulative radiation dose detection to be performed even in a case in which the valid blocks include a lot of defective blocks, since normal blocks adjacent to the valid blocks are set as the new valid blocks in a case in which most of the valid blocks are defective blocks. Note that normal blocks adjacent to the valid blocks may be set as new valid blocks in a case in which all of the valid blocks are defective blocks.

In a case in which all of the blocks, or a proportion of the valid blocks above a specific value are defective blocks, the CPU 26A of the cassette controller 26 may display a message on a display section of the electronic cassette 1 (not illustrated in the drawings) to the effect that cumulative radiation dose detection is not possible, or may transmit such a message to the console 230 using the wireless communication section 27. In a case in which the message is transmitted to the console 230, the message is displayed on the display 231 of the console 230. The imaging technician is able to act on this message, for example using a conventional radiation detection device, such as an ion chamber or the like, together with the electronic cassette 1 according to the present exemplary embodiment to detect the cumulative radiation dose.

As is clear from the above explanation, in the electronic cassette 1 according to the present exemplary embodiment, the blocks 62 containing plural radiation dose detection pixels 60B are arranged corresponding to the imaging target site, and radiation dose detection is performed treating each block 62 as a single pixel (sensor). In the electronic cassette 1 according to the present exemplary embodiment, the block size is set corresponding to the imaging target site in the block arrangement processing (see FIG. 10), thereby enabling radiation dose detection to be performed at a spatial resolution appropriate to the size of the imaging target site, for example. Moreover, in the electronic cassette 1 according to the present exemplary embodiment, block rearrangement is possible in a case in which defects occur in the arranged blocks 62. In the block rearrangement processing, the placement of the defective blocks can be moved by modifying the block size or by moving the position of the boundary lines L separating between the blocks. A contiguous normal block area of comparatively large surface area can accordingly be secured, thereby facilitating positioning of the imaging subject so as to avoid the defective blocks.

Note that in the above exemplary embodiment, an example is illustrated in which the sensors 13B configuring the radiation dose detection pixels 60B are connected directly to the signal lines 22, however a configuration is also possible in which the sensors 13B are connected to TFTs similarly to the imaging pixels 60A, and a timing for reading charges from the sensors 13B can be controlled by gate signals. In the exemplary embodiment described above, the pixel units 61 are configured by plural radiation dose detection pixels 60B connected to the same signal line, and the pixel units 61 configure the minimum units of the blocks, however the sensors 13B may be connected to TFTs such that timings for reading charges from the sensors 13B may be set freely. More flexible block arrangement is accordingly enabled since the minimum units of the blocks can accordingly be configured by a single radiation dose detection pixel 60B. Note that in such cases, the gate lines 21 that drive the TFTs 40 in the imaging pixels 60A, and the gate lines that drive the TFTs in the radiation dose detection pixels 60B are preferably configured as separate systems to each other, such that charges from the pixels 60A and 60B can be read independently of each other. In the exemplary embodiment described above, an example is illustrated in which the imaging pixels 60A and the radiation dose detection pixels 60B are connected through common signal lines 22, however the signal lines connected to the imaging pixels 60A and the signal lines connected to the radiation dose detection pixels 60B may be configured as separate systems.

Moreover, in the exemplary embodiment described above, cassette control such as gate driver control and block arrangement processing are performed by the CPU 26A, however, for example, specific programs may be read into a data processing device such as a programmable gate Integrated Circuit (IC), for example a Field Programmable Gate Array (FPGA), causing the data processing device to function as the cassette controller 26.

In the exemplary embodiment described above, an example is illustrated in which the electronic cassette 1 detects the cumulative radiation dose of the radiation irradiated from the radiation source 211, however configuration may be made such that the electronic cassette 1 intermittently outputs momentary radiation doses of the irradiated radiation. In such cases, the cumulative radiation dose of the radiation irradiated from the radiation source is computed on the signal receiving side.

In the exemplary embodiment described above, explanation has been given regarding a case in which the sensors 13A and 13B configuring the imaging pixels 60A and the radiation dose detection pixels 60B are configured including an organic photoelectric conversion material that generates charges on receiving light generated by the scintillator 30, however the present invention is not limited thereto, and may be made applied to a configuration in which the sensors 13A and 13B do not include an organic photoelectric conversion material. For example, configuration may include sensors 13A and 13B that employ a semiconductor such as amorphous selenium, and convert radiation directly into charges.

In the exemplary embodiment described above, explanation has been given regarding a case in which wireless communication is performed between the electronic cassette 1 and the console 230, and between the radiation generator 210 and the console 230, however the present invention is not limited thereto. For example, at least one of the above may be performed using wired communication.

In the exemplary embodiment described above, an example is illustrated in which the radiation dose detection pixels 60B are employed in automatic exposure control (AEC), however the radiation dose detection pixels 60B may also be employed to detect the start of radiation irradiation from the radiation source 211. The electronic cassette 1 is accordingly able to detect radiation irradiation start itself even without receiving instruction data from an external device instructing radiation irradiation start.

In the exemplary embodiment described above, explanation has been given regarding a case in which X-rays are employed as the radiation, however the present invention is not limited thereto. Another type of radiation, such as gamma radiation, may be employed as the radiation.

Embodiments of the present invention are described above, but the present invention is not limited to the embodiments as will be clear to those skilled in the art.

The disclosure of Japanese Patent Application No. 2012-218258 is incorporated in its entirety to the present specification by reference.

All cited documents, patent applications and technical standards mentioned in the present specification are incorporated by reference in the present specification to the same extent as if the individual cited document, patent application, or technical standard was specifically and individually indicated to be incorporated by reference.

What is claimed is:

1. A radiographic image capturing device comprising:
   a plurality of radiation dose detection pixels that respectively output signal values according to a dose of irradiated radiation;
   a determination unit that determines a presence or absence of defects, block-by-block, based on signal values of radiation dose detection pixels included in each of a plurality of blocks, which are arranged such that the respective blocks include at least a portion of the plurality of radiation dose detection pixels;
   a block rearrangement unit that performs block rearrangement to change the arrangement of the plurality of blocks according to a determination result of the determination unit; and
   a detection unit that detects a dose of irradiated radiation based on signal values of each arranged block or of each rearranged block.

2. The radiographic image capturing device of claim 1, wherein the block rearrangement unit performs block rearrangement to change the arrangement of the plurality of blocks based on instruction input supplied in a case in which the determination unit has determined that a defect is present in any of the plurality of blocks.

3. The radiographic image capturing device of claim 1, wherein the block rearrangement unit changes a block size of each of the plurality of blocks.

4. The radiographic image capturing device of claim 1, wherein the block rearrangement unit moves inter-block boundaries defining each of the plurality of blocks, while maintaining a block size of each of the plurality of blocks.

5. The radiographic image capturing device of claim 1, further comprising:
a buffer region including a plurality of radiation dose detection pixels that are capable of configuring a portion of any block rearranged by the block rearrangement unit.

6. The radiographic image capturing device of claim 5, wherein the buffer region is provided at an outer periphery of a block group made up of the plurality of blocks.

7. The radiographic image capturing device of claim 1, further comprising:
imaging pixels that output signal values according to doses of irradiated radiation to capture a radiographic image; and
an identification unit that identifies an imaging target site to be imaged by the imaging pixels,
wherein each of the plurality of blocks has a block size according to the imaging target site identified by the identification unit.

8. The radiographic image capturing device of claim 1, further comprising:
a notification unit that notifies a placement of a defective block which has been determined to have a defect by the determination unit, or a placement of a normal block other than the defective block.

9. The radiographic image capturing device of claim 1, wherein the detection unit detects doses of irradiated radiation based only on signal values of normal blocks other than defective blocks which have been determined to have a defect by the determination unit.

10. The radiographic image capturing device of claim 1, further comprising:
a correction unit that corrects a signal value of a defective block which has been determined to have a defect by the determination unit, using a signal value of a normal block adjacent to the defective block.

11. A non-transitory computer readable storage medium storing a program that causes a computer to function as the determination unit, the block rearrangement unit, and the detection unit of the radiographic image capturing device of claim 1.

12. A method for detecting radiation doses, comprising:
determining a presence or absence of defects, block-by-block, based on signal values of radiation dose detection pixels included in each of a plurality of blocks, which are arranged such that the respective blocks include at least a portion of a plurality of radiation dose detection pixels that respectively output signal values according to a dose of irradiated radiation;
performing block rearrangement to change the arrangement of the plurality of blocks in a case in which a defect is determined to be present in any of the plurality of blocks; and
detecting a dose of irradiated radiation based on signal values of each arranged block or of each rearranged block.

* * * * *